United States Patent [19]

Capet et al.

[11] Patent Number: 5,716,936
[45] Date of Patent: Feb. 10, 1998

[54] PYRROLIDINE DERIVATIVES FOR THE TREATMENT OF CHOLECYSTOKININE AND GASTRINE-RELATED DISORDERS

[75] Inventors: Marc Capet, Thiais; Marie-Christine Dubroeucq, Les Bains, both of France

[73] Assignee: Rhone-Poulenc Rorer S.A., Antony, France

[21] Appl. No.: 750,653

[22] PCT Filed: Jun. 16, 1995

[86] PCT No.: PCT/FR95/00796

§ 371 Date: Dec. 18, 1996

§ 102(e) Date: Dec. 18, 1996

[87] PCT Pub. No.: WO95/35310

PCT Pub. Date: Dec. 28, 1995

[30] Foreign Application Priority Data

Jun. 20, 1994 [FR] France .................... 94/07540

[51] Int. Cl.⁶ .................... C07D 207/12; A61K 31/40

[52] U.S. Cl. ........................................ 514/19; 548/533
[58] Field of Search .......................... 548/533; 514/19

[56] References Cited

U.S. PATENT DOCUMENTS

| 4,593,102 | 6/1986 | Shanklin, Jr. |
| 4,642,348 | 2/1987 | Shanklin, Jr. |
| 5,610,144 | 3/1997 | Capet .................... 514/19 |

FOREIGN PATENT DOCUMENTS

WO9301167  1/1993  WIPO.

*Primary Examiner*—Robert Gerstl
*Attorney, Agent, or Firm*—Finnegan, Henderson, Farabow, Garrett & Dunner, L.L.P.

[57] ABSTRACT

Compounds of formula (I), in which R, $R_1$, $R_2$, $R_3$, $R_4$, $R_5$, $R_6$, and $R_7$ are as defined in the specification. The invention also concerns the salts of said compounds, the preparation thereof and the drugs containing same.

15 Claims, No Drawings

PYRROLIDINE DERIVATIVES FOR THE TREATMENT OF CHOLECYSTOKININE AND GASTRINE-RELATED DISORDERS

This application is a 371 of PCT/FR9500796 filed Jun. 16, 1995.

The present invention relates to derivatives of formula:

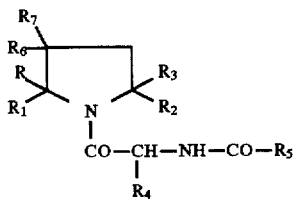

to their salts, to their preparation and to the medicaments containing them.

In formula (I),

R represents an alkyl radical containing 1 to 12 carbon atoms, in a straight or branched chain and optionally mono- or polyunsaturated, a cycloalkyl radical containing 3 to 12 carbon atoms and optionally mono- or polyunsaturated, a polycycloalkyl radical containing 6 to 12 carbon atoms and optionally mono- or polyunsaturated, a phenylalkyl radical in which the phenyl ring is optionally substituted (with one or more substituents chosen from alkyl and alkoxy radicals or halogen atoms), a diphenylalkyl or cinnamyl radical, a pyridyl radical optionally substituted with one or more alkyl radicals, a furyl radical optionally substituted with one or more alkyl radicals, a thienyl radical optionally substituted with one or more alkyl radicals, a quinolyl radical optionally substituted with one or more alkyl radicals, a naphthyl radical optionally substituted with one or more alkyl radicals, an indolyl radical optionally substituted with one or more alkyl radicals or a phenyl radical optionally substituted with one or more substituents chosen from halogen atoms and alkyl, alkoxy, hydroxyl, nitro, amino, monoalkylamino, dialkylamino, alkoxycarbonyl, —CO—$NR_8R_9$, —NH—CO—$CH_3$, trifluoromethyl and trifluoromethoxy radicals, $R_1$ represents a hydrogen atom or an alkyl radical, $R_2$ represents a chain —$(CH_2)_n$—CO—$R_{10}$, —$(CH_2)_m$—O—CO—$R_{11}$ or —$(CH_2)_m$—$NR_{12}R_{13}$ or an oxazolinyl radical optionally substituted with one or more alkyl radicals or a 3-alkyloxadiazolyl radical, $R_3$ represents a hydrogen atom or an alkyl radical, $R_4$ represents a hydrogen atom or an alkyl radical, $R_5$ represents a phenyl radical (optionally substituted with one or more substituents chosen from halogen atoms and alkyl, alkoxy and alkylthio radicals), a naphthyl, indolyl or quinolyl radical, or a phenylamino radical in which the phenyl ring is optionally substituted with one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-$SO_3H$ (in salt form), —CH=CH-alk', —C(=NOH)—COOX, —S-alk-COOX, —SO-alk-COOX, —$SO_2$-alk-COOX, —O—$CH_2$-alk'-COOX, —CX=N—O-alk-COOX, -alk-N(OH)—CO-alk, -alk-$SO_2H$, —$SO_2$—NH—CO—$R_{14}$, —$SO_2$—NH—$SO_2$—$R_{14}$, —CO—NH—CO—$R_{14}$, —CO—NH—$SO_2$—$R_{14}$, —$B(OH)_2$, —$C(NH_2)$=NOH, —$SO_2$—NH—$R_{15}$, —CO—NH—$R_{15}$,

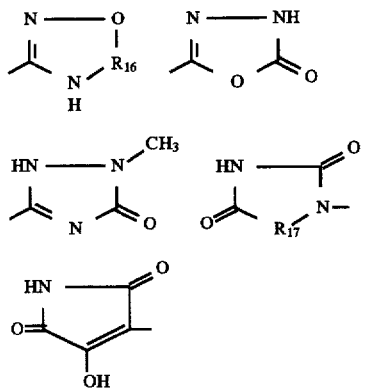

and 2,2-dimethyl-4,6-dioxo-1,3-dioxan-5-yl radicals, $R_6$ represents a hydrogen atom or an alkyl or phenylalkyl radical, $R_7$ represents an alkylsulphonyl radical, a radical —$SO_2$—$NR_8R_9$ or a phenylsulphonyl radical in which the phenyl ring is substituted with one or more substituents chosen from halogen atoms and alkyl, alkoxy, hydroxyl, nitro, amino, monoalkylamino, dialkylamino, acylamino, trifluoromethyl and trifluoromethoxy radicals, $R_8$ represents a hydrogen atom or an alkyl or phenylalkyl radical or a phenyl radical which is optionally substituted with one or more substituents chosen from halogen atoms and alkyl, alkoxy and alkylthio radicals, $R_9$ represents an alkyl or phenylalkyl radical or a phenyl radical which is optionally substituted with one or more substituents chosen from halogen atoms and alkyl, alkoxy and alkylthio radicals, or alternatively $R_8$ and $R_9$ form, together with the nitrogen atom to which they are attached, a saturated or unsaturated mono- or polycyclic heterocycle containing 4 to 9 carbon atoms and one or more hetero atoms (O, N) and is optionally substituted with one or more alkyl radicals, $R_{10}$ represents a hydroxyl, alkoxy, cycloalkyloxy, cycloalkylalkyloxy, phenyl or —$NR_{12}R_{13}$ radical, $R_{11}$ represents an alkoxy, cycloalkyloxy, cycloalkylalkyloxy, phenyl or —$NR_{12}R_{13}$ radical, $R_{12}$ represents a hydrogen atom or an alkyl, cycloalkylalkyl, cycloalkyl or phenylalkyl radical or a phenyl radical which is optionally substituted with one or more substituents chosen from halogen atoms and alkyl, alkoxy and alkylthio radicals, $R_{13}$ represents an alkyl, cycloalkylalkyl, cycloalkyl or phenylalkyl radical or a phenyl radical which is optionally substituted with one or more substituents chosen from halogen atoms and alkyl, alkoxy and alkylthio radicals, or alternatively $R_{12}$ and $R_{13}$ form, together with the nitrogen atom to which they are attached, a saturated or unsaturated mono- or polycyclic heterocycle containing 4 to 9 carbon atoms and one or more hetero atoms (O, N, S) and optionally substituted with one or more alkyl radicals, $R_{14}$ represents an alkyl, cycloalkyl or trifluoromethyl radical or a phenyl radical which is optionally substituted with one or more substituents chosen from cyano, alkoxy, nitro and amino radicals and halogen atoms, $R_{15}$ represents a 5-tetrazolyl radical, $R_{16}$ represents C=O or S=O, $R_{17}$ represents O or C=O, n is equal to 0, 1 or 2, m is equal to 1 or 2, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical.

In the preceding definitions and in those which will be mentioned below, except where otherwise mentioned, the alkyl, alkylene and alkoxy radicals and the alkyl, alkylene and alkoxy portions contain 1 to 4 carbon atoms in a straight or branched chain, the acyl radicals or portions contain 2 to 4 carbon atoms and the cycloalkyl radicals and portions contain 3 to 6 carbon atoms.

When R represents an unsaturated alkyl radical, the latter is preferably an isopropylidene radical.

When R represents a cycloalkyl radical, the latter is preferably a cyclohexyl radical.

When R represents an unsaturated cycloalkyl radical, the latter is preferably a tetrahydrophenyl, cyclopentadienyl or dihydrophenyl radical.

When R represents a polycycloalkyl radical, the latter is preferably a norbornyl or adamantyl radical.

When R represents an unsaturated polycycloalkyl radical, the latter is preferably a norbornenyl radical.

When $R_8$ and $R_9$ form, together with the nitrogen atom to which they are attached, a heterocycle, the latter is preferably a piperidino ring optionally substituted with one or more alkyl, morpholino or 1,2,3,4-tetrahydroquinoline radicals.

When $R_{12}$ and $R_{13}$ form, together with the nitrogen atom to which they are attached, a heterocycle, the latter is preferably a piperidino, perhydro-1-azepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino or 1-indolinyl ring system, it being possible for these ring systems optionally to be substituted with at least one alkyl radical.

The compounds of formula (I) containing one or more asymmetric centres have isomeric forms. These isomers also form part of the invention.

The compounds of formula (I) for which $R_5$ represents a phenylamino radical in which the phenyl ring is optionally substituted may be prepared by the action of a reactive derivative of carbamic acid, optionally obtained in situ by the action of a reactive derivative of carbonic acid chosen from N,N'-carbonyldiimidazole, phosgene, diphosgene, triphosgene and p-nitrophenyl chloroformate on a derivative of formula:

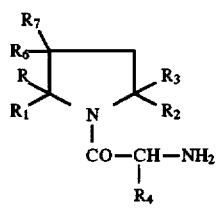

in which R, $R_1$, $R_2$, $R_3$, $R_4$, $R_6$ and $R_7$ have the same meanings as in formula (I), on an aniline in which the phenyl ring is optionally substituted with one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-SO₃H (in salt form), —CH=CH-alk', —C(=NOH)—COOX, —S-alk-COOX, —SO-alk-COOX, —SO₂-alk-COOX, —O—CH₂-alk'-COOX, —CX=N—O-alk-COOX, -alk-N(OH)—CO-alk, -alk-SO₂H, —SO₂—NH—CO—$R_{14}$, —SO₂—NH—SO₂—$R_{14}$, —CO—NH—CO—$R_{14}$, —CO—NH—SO₂—$R_{14}$, —B(OH)₂, —C(NH₂)=NOH, —SO₂—NH—$R_{15}$, —CO—NH—$R_{15}$,

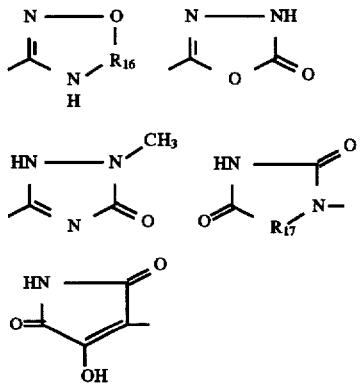

and 2,2-dimethyl-4,6-dioxo-1,3-dioxan-5-yl radicals, alk, alk', X, $R_{14}$, $R_{15}$, $R_{16}$ and $R_{17}$ having the same meanings as in formula (I).

This reaction is generally carried out in an inert solvent such as tetrahydrofuran, N,N-dimethylformamide, a chlorinated solvent (chloroform or 1,2-dichloroethane for example) or an aromatic solvent (benzene or toluene for example), at a temperature between 20° C. and the boiling point of the solvent.

The reactive derivative of carbamic acid may be obtained under the same temperature and solvent conditions.

The derivatives of formula (II) may be obtained by deprotection of a derivative of formula:

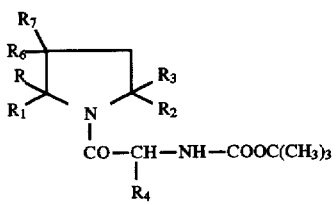

in which R, $R_1$, $R_2$, $R_3$, $R_4$, $R_6$ and $R_7$ have the same meanings as in formula (I).

This deprotection is preferably carried out using iodotrimethylsilane, in an inert solvent such as a chlorinated solvent (chloroform or 1,2-dichloroethane for example) or acetonitrile, at a temperature between 15° and 40° C.

The derivatives of formula (III) for which $R_2$ represents a chain $-(CH_2)_n-CO-R_{10}$, $R_{10}$ represents an alkoxy, cycloalkyloxy, cycloalkylalkyloxy, phenyl or $-NR_{12}R_{13}$ radical and $R_7$ represents an alkylsulphonyl radical, a radical $-SO_2-NR_8R_9$ or a phenylsulphonyl radical in which the phenyl ring is substituted with one or more substituents chosen from halogen atoms and alkyl, alkoxy, nitro, amino, monoalkylamino, dialkylamino, acylamino, trifluoromethyl and trifluoromethoxy radicals, may be obtained by the action of a derivative of formula:

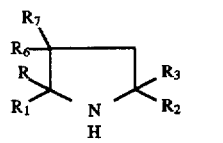

in which R, $R_1$, $R_3$ and $R_6$ have the same meanings as in formula (I) and $R_2$ and $R_7$ have the same meanings as above, on an acid of formula:

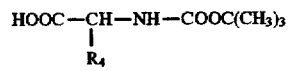

in which $R_4$ is defined as in formula (I).

This reaction is carried out in an inert solvent such as acetonitrile, tetrahydrofuran or a chlorinated solvent, in the presence of a coupling agent used in peptide chemistry such as a carbodiimide (N,N'-dicyclohexylcarbodiimide for example) or an alkyl chloroformate, at a temperature between 10° and 40° C.

The derivatives of formula (V) may be obtained according to the usual methods for the protection of amino acids.

The derivatives of formula (IV) for which $R_2$ represents a chain $-(CH_2)_n-CO-R_{10}$ and n is equal to 0 may be obtained by reaction of a derivative of formula:

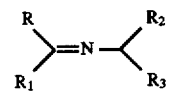

in which R, $R_1$ and $R_3$ have the same meanings as in formula (I) and $R_2$ represents a chain $-(CH_2)_n-CO-R_{10}$, n is equal to 0, $R_{10}$ represents an alkoxy, cycloalkyloxy, cycloalkylalkyloxy, phenyl or $-NR_{12}R_{13}$ radical and $R_{12}$ and $R_{13}$ have the same meanings as in formula (I), with a derivative of formula:

in which $R_6$ has the same meanings as in formula (I) and $R_7$ represents an alkylsulphonyl radical, a radical $-SO_2-$ $NR_8R_9$ or a phenylsulphonyl radical in which the phenyl ring is substituted with one or more substituents chosen from halogen atoms and alkyl, alkoxy, nitro, amino, monoalkylamino, dialkylamino, acylamino, trifluoromethyl and trifluoromethoxy radicals, and $R_8$ and $R_9$ have the same meanings as in formula (I).

This reaction is carried out in an inert solvent such as acetonitrile, tetrahydrofuran or toluene, in the presence of a metal salt such as silver acetate, lithium bromide, magnesium bromide, sodium iodide or zinc iodide, and in the presence of a nitrogen-containing base such as triethylamine, at a temperature between 0° C. and the boiling point of the reaction medium.

The derivatives of formula (VII) are commercially available or may be obtained by application or adaptation of the methods described by N. O. Brace, J. Org. Chem., 58, 4506 (1993), B. E. Love, Li Chao, Synth. Commun., 23, 3073 (1993) or J. Chanet-Rey et al., Heterocycles, 26, 101 (1987).

The derivatives of formula (VI) may be obtained by the action of a ketone $R-CO-R_1$ in which R and $R_1$ have the same meanings as in formula (I), on an amine $H_2N-CH(R_2)R_3$ in which $R_2$ has the same meanings as in formula (VI) and $R_3$ has the same meanings as in formula (I).

This reaction is generally carried out either using a dehydrating agent such as 4 Å molecular sieves, in an inert solvent such as dichloromethane, at a temperature between 0° C. and the boiling point of the reaction medium, or by azeotropic distillation of the water in an aromatic solvent such as toluene, optionally in the presence of an acid such as paratoluenesulphonic acid.

The derivatives of formula (IV) for which $R_2$ represents a chain $-(CH_2)_n-CO-R_{10}$, n is equal to 0 and $R_7$ represents a substituted phenylsulphonyl radical, may also be obtained by adaptation of the methods described by S. Kanemasa et al., Bull. Chem. Soc. Japan, 62, 869 (1982); D. A. Barr et al., J. Chem. Soc. Perkin Trans. I, 1550 (1989) and O. Tsuge et al., J. Org. Chem., 53, 1384 (1988).

The derivatives of formula (IV) for which $R_2$ represents a chain $-(CH_2)_n-CO-R_{10}$ and n is equal to 1 or 2 may be obtained by adaptation of the methods described by S. Rossett et al., Tetrahedron Lett., 32, 7521 (1991); T. Gallagher et al., J. Chem. Soc. Perkin Trans. I, 2193 (1991) and J. F. W. Keana, J. Org. Chem., 48, 2644 (1983).

The derivatives of formula (IV) for which $R_2$ represents a radical $-(CH_2)_n-CO-R_{10}$ and $R_{10}$ represents a radical $-NR_{12}R_{13}$ may also be obtained by the action of an amine $HNR_{12}R_{13}$, in which $R_{12}$ and $R_{13}$ have the same meanings as in formula (I), on a corresponding derivative of formula (IV) for which $R_2$ represents a radical $-(CH_2)_n-CO-R_{10}$ and $R_{10}$ represents a hydroxyl radical, according to the methods described in the examples. The process is generally performed in the presence of a coupling agent used in peptide chemistry such as a carbodiimide (for example N,N'-dicyclohexylcarbodiimide) or N,N'-carbonyldiimidazole, in an inert solvent such as an ether (tetrahydrofuran or dioxane for example), an amide (dimethylformamide) or a chlorinated solvent (methylene chloride, 1,2-dichloroethane or chloroform for example) at a temperature between 0° C. and the reflux temperature of the reaction mixture). It may be necessary to introduce a protective group for the amine function of the compound of formula (IV), such as those protective groups described by T. W. Greene, Protective Groups in Organic Synthesis, John Wiley and Sons, New York.

The derivatives of formula (IV) for which $R_2$ represents a radical $-(CH_2)_n-CO-R_{10}$ and $R_{10}$ represents a hydroxyl radical may also be obtained by hydrolysis of a corresponding derivative of formula (IV) for which $R_2$ represents a radical —$(CH_2)_n$—CO—$R_{10}$ and $R_{10}$ represents an alkoxy radical. It is advantageous to carry out the hydrolysis using a base such as sodium hydroxide, potassium hydroxide or lithium hydroxide, in an inert solvent such as tetrahydrofuran, dioxane, water, methanol or a mixture of these solvents, at a temperature between 20° C. and 40° C.

The derivatives of formula (III) for which $R_2$ represents a chain —$(CH_2)_n$—CO—$R_{10}$ and $R_{10}$ represents a hydroxyl radical may be obtained by hydrolysis or, depending on the case, hydrogenolysis of the corresponding esters of formula (III).

When alkyl or phenylalkyl esters are used, it is advantageous to carry out the hydrolysis using a base such as sodium hydroxide, potassium hydroxide or lithium hydroxide, in an inert solvent such as tetrahydrofuran, dioxane, water, methanol or a mixture of these solvents, at a temperature between 20° C. and 40° C. When phenylalkyl esters are used, it may also be advantageous to carry out a hydrogenolysis using hydrogen or ammonium formate in the presence of a catalyst such as palladium-on-charcoal, in a solvent such as methanol or ethyl acetate.

The derivatives of formula (III) for which $R_2$ represents a chain —$(CH_2)_m$—O—CO—$R_{11}$ may be obtained by reaction of a derivative of formula:

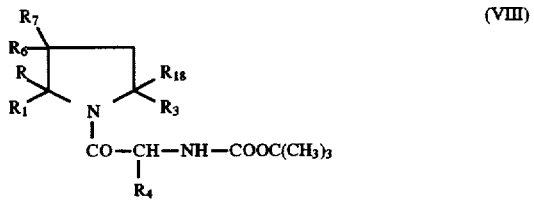

(VIII)

in which R, $R_1$, $R_3$, $R_4$, $R_6$ and $R_7$ have the same meanings as in formula (I) and $R_{18}$ represents a chain —$(CH_2)_m$—OH, either with a halide of formula Hal-CO—$R_{11}$, in which Hal represents a halogen atom and $R_{11}$ has the same meanings as in formula (I), or with an anhydride of formula $(R_{11}CO)_2O$ in which $R_{11}$ has the same meanings as in formula (I).

This reaction is carried out in an inert solvent such as a chlorinated solvent, in the presence of a trialkylamine, at a temperature between 20° C. and the boiling point of the reaction medium.

The derivatives of formula (VIII) may be obtained by reduction of a corresponding derivative of formula (III) for which $R_2$ represents a chain —$(CH_2)_n$—CO—$R_{10}$, n is equal to 0 or 1 and $R_{10}$ represents a hydroxyl or alkoxy radical.

This reaction is carried out in an alcohol (methanol, ethanol or tert-butanol), tetrahydrofuran or a mixture of these solvents, in the presence of sodium borohydride or diborane, at a temperature between 20° C. and the boiling point of the reaction medium.

The derivatives of formula (III) for which $R_2$ represents a chain —$(CH_2)_m$—O—CO—$R_{11}$, $R_{11}$ represents a radical —$NR_{12}R_{13}$ and $R_{12}$ represents a hydrogen atom, may also be obtained by condensation of a derivative of formula (VIII), in which $R_{18}$ represents a chain —$(CH_2)_m$—OH, with an isocyanate of formula $R_{13}NCO$ in which $R_{13}$ has the same meanings as in formula (I).

This reaction is carried out in an inert solvent such as a chlorinated solvent, tetrahydrofuran or N,N-dimethylformamide, optionally in the presence of a catalytic amount of an alkali metal alkoxide, at a temperature between 20° C. and the boiling point of the reaction medium.

The derivatives of formula (III) for which $R_2$ represents a radical —$(CH_2)_m$—$NR_{12}R_{13}$ may be obtained by the action of an amine $HNR_{12}R_{13}$, in which $R_{12}$ and $R_{13}$ have the same meanings as in formula (I), on a derivative of formula (VIII) in which $R_{18}$ represents a radical —$(CH_2)_m$—O—$SO_2$—$CH_3$.

This reaction is generally carried out either in the presence of a large excess of amine, at a temperature between 0° and 10° C., or, when the amine hydrochloride is used, in a chlorinated solvent, in the presence of a trialkylamine, at a temperature between 20° C. and the boiling point of the reaction medium.

The derivatives of formula (VIII) in which $R_{18}$ represents a radical —$(CH_2)_m$—O—$SO_2$—$CH_3$ may be obtained by reaction of a corresponding derivative of formula (VIII), for which $R_{18}$ represents a radical —$(CH_2)_m$—OH, with methanesulphonyl chloride.

This reaction is generally carried out in an inert solvent such as acetonitrile or methylene chloride, in the presence of triethylamine, at a temperature between 0° C. and the boiling point of the reaction medium.

The derivatives of formula (III) for which $R_2$ represents a radical —$(CH_2)_n$—CO—$R_{10}$ and $R_{10}$ represents a hydroxyl radical may be obtained by saponification of a corresponding derivative of formula (III) for which $R_{10}$ represents an alkoxy radical.

This reaction is carried out in inert solvents such as methanol, dioxane, tetrahydrofuran and water or a mixture of these solvents, in the presence of a base such as sodium hydroxide, potassium hydroxide or lithium hydroxide, at a temperature between 0° and 25° C.

The derivatives of formula (III), for which $R_2$ represents a radical —$(CH_2)_n$—CO—$R_{10}$ and $R_{10}$ represents an alkoxy, cycloalkoxy or cycloalkylalkyloxy radical, may be obtained by esterification of the corresponding derivatives of formula (III) for which $R_2$ represents a radical —$(CH_2)_n$—CO—$R_{10}$ and $R_{10}$ represents a hydroxyl radical.

This reaction is preferably carried out using an alcohol $R_{19}$—OH in which $R_{19}$ represents an alkyl, cycloalkyl or cycloalkylalkyl radical, in the presence of tosyl chloride, in pyridine, at a temperature between 0° and 25° C.

The derivatives of formula (III), for which $R_2$ represents a radical —$(CH_2)_n$—CO—$R_{10}$ and $R_{10}$ represents a phenyl radical, may be obtained by the action of a corresponding derivative of formula (III), for which $R_2$ represents a radical —$(CH_2)_n$—CO—$R_{10}$ and $R_{10}$ represents an alkoxy radical, with phenylmagnesium bromide.

This reaction is preferably carried out in an inert solvent such as tetrahydrofuran or ethyl ether, at a temperature between −70° C. and the boiling point of the reaction medium.

The derivatives of formula (III) for which $R_2$ represents an optionally substituted oxazolinyl radical may be obtained by the action of a corresponding derivative of formula (III), for which $R_2$ represents a radical —$(CH_2)_n$—CO—$R_{10}$, n is equal to 0 and $R_{10}$ represents a hydroxyl radical, on 2-aminoethanol optionally substituted with one or more alkyl radicals.

This reaction is carried out in an inert solvent such as toluene by removing the water formed, at the boiling point of the reaction medium.

The derivatives of formula (III) for which $R_2$ represents a 3-alkyloxadiazolyl radical may be obtained by the action of a corresponding derivative of formula (III), for which $R_2$ represents a radical —$(CH_2)_n$—CO—$R_{10}$, n is equal to 0 and $R_{10}$ represents an alkoxy radical, on an alkylamidoxime.

This reaction is carried out in an inert solvent such as tetrahydrofuran, in the presence of sodium hydride, at a temperature between 25° C. and the boiling point of the reaction medium.

The derivatives of formula (III) for which $R_2$ represents a chain —$(CH_2)_n$—CO—$R_{10}$ and $R_{10}$ represents a radical —$NR_{12}R_{13}$ may be obtained by the action of a corresponding derivative of formula (III), for which $R_{10}$ represents a hydroxyl radical or a reactive derivative of this acid, on an amine of formula $HNR_{12}R_{13}$ in which $R_{12}$ and $R_{13}$ have the same meanings as in formula (I).

When the acid is used, the process is performed in the presence of a coupling agent used in peptide chemistry such as a carbodiimide (for example N,N'-dicyclohexylcarbodiimide) or N,N'-carbonyldiimidazole, in an inert solvent such as an ether (tetrahydrofuran or dioxane for example), an amide (N,N-dimethylformamide) or a chlorinated solvent (methylene chloride, 1,2-dichloroethane or chloroform for example), at a temperature between 0° C. and the reflux temperature of the reaction mixture.

When a reactive derivative of the acid is used, it is possible to react the anhydride, a mixed anhydride or an ester (which may be chosen from activated or non-activated esters of the acid).

The process is then performed either in an organic medium, optionally in the presence of an acid acceptor such as a nitrogen-containing organic base (trialkylamine, pyridine, 1,8-diazabicyclo[5.4.0]undec-7-ene or 1,5-diazabicyclo[4.3.0]non-5-ene for example), in a solvent as mentioned above, or a mixture of these solvents, at a temperature between 0° C. and the reflux temperature of the reaction mixture, or in a two-phase aqueous-organic medium in the presence of an alkali metal or alkaline-earth metal base (sodium hydroxide or potassium hydroxide) or an alkali metal or alkaline-earth metal carbonate or bicarbonate, at a temperature between 0° and 40° C.

The anilines, which may be substituted, are commercially available or may be obtained by application or adaptation of the methods described by R. Schröter, Methoden der organischen Chemie, Houben Weyl, Vol. XI/1, p 360; G. J. Esselen et al., J. Am. Chem. Soc., 36, 322 (1914); G. Adriant et al., Bull. Soc. Chim. Fr., 1511 (1970); W. A. Jacobs et al., J. Am. Chem. Soc., 39, 2438 (1917) and J. Am. Chem. Soc. 39, 1438 (1917) and in the examples.

The compounds of formula (I), for which $R_5$ represents a phenylamino radical in which the phenyl ring is optionally substituted with one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH=CH-alk', -alk-O-alk, trifluoromethylsulphonamido, -alk-SO$_3$H (in salt form), —O-alk-COOX, —CH=CH—COOX, —CO—COOX, —S-alk-COOX, —SO-alk-COOX, —SO$_2$-alk-COOX, —CH$_2$-alk'-COOX, —CX=N—O-alk-COOX, -alk-COOX and -alk'-COOX radicals in which X is an alkyl or phenylalkyl radical, may also be prepared by the action of a derivative of formula (II), in which R, $R_1$, $R_2$, $R_3$, $R_4$, $R_6$ and $R_7$ have the same meanings as in formula (I), on a phenyl isocyanate in which the phenyl ring is optionally substituted with one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH=CH-alk', -alk-O-alk, trifluoromethylsulphonamido, -alk-SO$_3$H (in salt form), —O-alk-COOX, —CH=CH—COOX, —CO—COOX, —S-alk-COOX, —SO-alk-COOX, —SO$_2$-alk-COOX, —O—CH$_2$-alk'-COOX, —CX=N—O-alk-COOX, -alk-COOX and -alk'-COOX radicals in which X is an alkyl or phenylalkyl radical and alk and alk' have the same meanings as in formula (I).

This reaction is generally carried out in an inert solvent such as tetrahydrofuran, N,N-dimethylformamide, a chlorinated solvent (chloroform or 1,2-dichloroethane for example) or an aromatic solvent (benzene or toluene for example), at a temperature between 10° C. and the boiling point of the solvent.

The phenyl isocyanates are commercially available or may be obtained by application or adaptation of the methods described by R. Richter et al., The Chemistry of Cyanate and their thio derivatives, S. Patai, part 2, Wiley New York (1977) and in the examples.

The compounds of formula (I) for which $R_5$ represents a phenyl radical which is optionally substituted, or a naphthyl, indolyl or quinolyl radical, may be prepared by the action of a derivative of formula (II), in which R, $R_1$, $R_2$, $R_3$, $R_4$, $R_6$ and $R_7$ have the same meanings as in formula (I), on an acid of formula HOOC—$R_5$ in which $R_5$ has the same meanings as above or a reactive derivative of this acid.

When the acid is used, the process is performed in the presence of a coupling agent used in peptide chemistry such as a carbodiimide (for example N,N'-dicyclohexylcarbodiimide) or N,N'-carbonyldiimidazole, in an inert solvent such as an ether (tetrahydrofuran or dioxane for example), an amide (N,N-dimethylformamide) or a chlorinated solvent (methylene chloride, 1,2-dichloroethane or chloroform for example) at a temperature between 0° C. and the reflux temperature of the reaction mixture.

When a reactive derivative of the acid is used, it is possible to react the anhydride, a mixed anhydride or an ester (which may be chosen from activated or non-activated esters of the acid).

The process is then performed either in an organic medium, optionally in the presence of an acid acceptor such as a nitrogen-containing organic base (trialkylamine, pyridine, 1,8-diazabicyclo[5.4.0]undec-7-ene or 1,5-diazabicyclo[4.3.0]non-5-ene for example), in a solvent as mentioned above, or a mixture of these solvents, at a temperature between 0° C. and the reflux temperature of the reaction mixture, or in a two-phase aqueous-organic medium in the presence of an alkali metal or alkaline-earth metal base (sodium hydroxide or potassium hydroxide) or an alkali metal or alkaline-earth metal carbonate or bicarbonate, at a temperature between 0° and 40° C.

The compounds of formula (I), for which $R_5$ represents a phenylamino radical in which the phenyl ring is substituted with a carboxyl, -alk-COOX, —O-alk-COOX, -alk'-COOX, —CH=CH—COOX, —CO—COOX, —S-alk-COOX, —SO-alk-COOX, —SO$_2$-alk-COOX, —C(=NOH)—COOX, —O—CH$_2$-alk'-COOX or —CX=N—O-alk-COOX radical and X represents a hydrogen atom, may also be prepared by hydrolysis or, depending on the case, hydrogenolysis of the corresponding esters of formula (I) for which X represents an alkyl or phenylalkyl radical.

When the alkyl or phenylalkyl esters are used, it is advantageous to carry out the hydrolysis using a base such as sodium hydroxide, potassium hydroxide or lithium hydroxide, in an inert solvent such as tetrahydrofuran, dioxane, water, methanol or a mixture of these solvents, at a temperature between 20° C. and 40° C. When phenylalkyl esters are used, it may also be advantageous to carry out a hydrogenolysis using hydrogen or ammonium formate in the presence of a catalyst such as palladium-on-charcoal, in a solvent such as methanol or ethyl acetate. When tert-butyl esters are used, it is advantageous to carry out the hydrolysis using an acid such as trifluoroacetic acid.

The compounds of formula (I), for which $R_5$ represents a phenylamino radical in which the phenyl ring is substituted with a hydroxyiminoalkyl or alkoxyiminoalkyl radical, may also be prepared by the action of the corresponding compound of formula (I), for which $R_5$ represents a phenylamino radical in which the phenyl ring is substituted with an acyl radical, on a derivative of formula:

$$H_2N—OR_{20} \quad (IX)$$

in which $R_{20}$ represents a hydrogen atom or an alkyl radical.

This reaction is generally carried out in an inert solvent such as an alcohol (methanol or ethanol for example), water or a mixture of these solvents, at the boiling point of the solvent, and optionally in the presence of a base such as pyridine.

The compounds of formula (I), for which $R_2$ represents a chain —$(CH_2)_n$—CO—$R_{10}$, $R_{10}$ represents an alkoxy, cycloalkyloxy, cycloalkylalkyloxy or phenyl radical or a radical —$NR_{12}R_{13}$, $R_7$ represents an alkylsulphonyl radical, a radical —$SO_2$—$NR_8R_9$ or a phenyl sulphonyl radical in which the phenyl ring is substituted with one or more substituents chosen from halogen atoms and alkyl, alkoxy, hydroxyl, nitro, amino, monoalkylamino, dialkylamino, acylamino, trifluoromethyl and trifluoromethoxy radicals and $R_5$ represents a phenyl radical which is optionally substituted, a naphthyl, indolyl or quinolyl radical or phenylamino radical in which the phenyl ring is optionally substituted with one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH=CH-alk', -alk-O-alk, trifluoromethylsulphonamido, -alk-$SO_3H$ (in salt form), —O-alk-COOX, —CH=CH—COOX, —CO—COOX, —S-alk-COOX, —SO-alk-COOX, —$SO_2$-alk-COOX, —O—$CH_2$-alk'-COOX, —CX=N—O-alk-COOX, -alk-COOX or -alk'-COOX radicals in Which X is an alkyl or phenylalkyl radical, may also be prepared by the action of a derivative of formula (IV) in which $R_2$ and $R_7$ have the same meanings as above and R, $R_1$, $R_3$ and $R_6$ have the same meanings as in formula (I), on an acid of formula:

$$HOOC—CH—NH—CO—R_5 \quad (X)$$
$$\quad |$$
$$\quad R_4$$

in which $R_5$ has the same meanings as above, or a reactive derivative of this acid, and $R_4$ has the same meanings as in formula (I).

This reaction is preferably carried out in the presence of a coupling agent used in peptide chemistry such as a carbodiimide, in a solvent such as acetonitrile, tetrahydrofuran or a chlorinated solvent, or using thionyl chloride in dichloromethane, at a temperature between 10° C. and the boiling point of the solvent.

The acids of formula (X) may be obtained by application or adaptation of the method described by J. R. Johnson et al., J. Am. Chem. Soc., 69, 2370 (1947) or, for the compounds for which $R_5$ represents an optionally substituted phenylamino radical, by the action of a phenyl isocyanate in which the phenyl ring is optionally substituted with one or more substituents chosen from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH=CH-alk', -alk-O-alk, trifluoromethylsulphonamido, -alk-$SO_3H$ (in salt form), —O-alk-COOX, —CH=CH—COOX, —CO—COOX, —S-alk-COOX, —SO-alk-COOX, —$SO_2$-alk-COOX, —O—$CH_2$-alk'-COOX, —CX=N—O-alk-COOX, -alk-COOX and -alk'-COOX radicals in which X is an alkyl or phenylalkyl radical, on a derivative of formula:

$$HOOC—CH—NH_2 \quad (XI)$$
$$\quad |$$
$$\quad R_4$$

in which $R_4$ has the same meanings as in formula (I).

This reaction is generally carried out in aqueous solution in the presence of a base such as an alkali metal bicarbonate, or in aqueous dioxane, at a temperature in the region of 20° C.

The compounds of formula (I) for which $R_7$ represents a phenylsulphonyl radical in which the phenyl is substituted with an amino radical may also be prepared by reduction of the corresponding compounds of formula (I) for which $R_7$ represents a phenylsulphonyl radical in which the phenyl is substituted with a nitro radical.

This reduction is generally carried out under a pressure of hydrogen (preferably 130 kPa), in the presence of a hydrogenation catalyst such as palladium-on-charcoal, in an inert solvent such as an alcohol (ethanol for example), at a temperature in the region of 20° C.

The compounds of formula (I) for which $R_7$ represents a phenylsulphonyl radical in which the phenyl is substituted with a monomethylamino or dimethylamino radical may also be prepared by methylation of the corresponding compounds of formula (I) for which $R_7$ represents a phenylsulphonyl radical in which the phenyl is substituted with an amino radical.

This reaction is carried out using formaldehyde, under a hydrogen pressure (preferably 130 kPa), in the presence of a hydrogenation catalyst such as palladium-on-charcoal in an inert solvent such as an alcohol (ethanol for example), at a temperature in the region of 20° C.

It is understood by those skilled in the art that, in order to carry out the processes according to the invention which are described above, it may be necessary, in order to avoid side reactions, to introduce protective groups for the amine, alcohol, acid and ketone functions such as those described by T. W. Greene, Protective Groups in Organic Synthesis, John Wiley and Sons, New York. For example, the amine functions may be blocked in the tert-butyl or methyl carbamate form and then regenerated using iodotrimethylsilane, or in the form of benzyl carbamates and then regenerated by hydrogenation after the process according to the invention has been carried out. The alcohol functions may, for example, be blocked in the form of benzoate and then regenerated by hydrolysis in an alkaline medium after the process according to the invention has been carried out. The ketone functions may be blocked in the form of 1,3-dioxolane and then regenerated using a hydrochloric acid-acetic acid mixture.

The enantiomers of the compounds of formula (I) containing at least one asymmetric site may be obtained by resolution of the racemic mixtures, for example by chromatography on a chiral column or by synthesis starting with chiral precursors.

The compounds of formula (I) may be purified by the usual known methods, for example by crystallization, chromatography or extractions.

The compounds of formula (I) containing a basic residue may optionally be converted into addition salts with an inorganic or organic acid by the action of such an acid in an organic solvent such as an alcohol, a ketone, an ether or a chlorinated solvent.

The compounds of formula (I) containing an acidic residue may optionally be converted into metal salts or into addition salts with nitrogen-containing bases according to methods that are known per se. These salts may be obtained by the action of a metal base (an alkali metal or alkaline-earth metal base for example), ammonia, an amine or an amine salt on a compound of formula (I), in a solvent. The salt formed is separated by the usual methods.

These salts also form part of the invention.

As examples of pharmaceutically acceptable salts, there may be mentioned the addition salts with inorganic or organic acids (such as acetate, propionate, succinate, benzoate, fumarate, maleate, oxalate, methanesulphonate, isethionate, theophyllineacetate, salicylate, methylenebis-β-oxynaphthoate, hydrochloride, sulphate, nitrate and phosphate), salts with alkali metals (sodium, potassium or lithium) or with alkaline-earth metals (calcium or magnesium), the ammonium salt, and salts of nitrogen-containing bases (ethanolamine, trimethylamine, methylamine, benzylamine, N-benzyl-β-phenethylamine, choline, arginine, leucine, lysine and N-methyl glucamine).

The compounds of formula (I) have advantageous pharmacological properties. These compounds possess a strong affinity for cholecystokinin (CCK) receptors and gastrin receptors and are thus useful in the treatment and prevention of disorders linked to CCK and to gastrin occurring in the nervous system and in the gastrointestinal system.

Hence, these compounds may be used for the treatment or prevention of psychosis, anxiety disorders, depression, neurodegeneration, panic attacks, Parkinson's disease, tardive dyskinesia, irritable bowel syndrome, acute pancreatitis, ulcers, intestinal motility disorders and certain CCK-sensitive tumours, as appetite regulators, in the withdrawal from chronic treatments and alcohol or drug abuse, and as a constrictor of the pupil of the eye.

These compounds also have a potentiating effect on the analgesic activity of narcotic and non-narcotic drugs. In addition, they may have an intrinsic analgesic effect.

Moreover, the compounds having a strong affinity for the CCK receptors modify the capacity for memorization. Consequently, these compounds may be effective in memory disorders.

The affinity of the compounds of formula (I) for the CCK receptors was determined according to a technique based on that of A. Saito et al. (J. Neuro. Chem., 37, 483–490 (1981)) in the cerebral cortex and in the pancreas.

In these tests, the $IC_{50}$ of the compounds of formula (I) is generally below or equal to 2000 nM.

Moreover, it is known that the products which recognize the CCK central receptors have a similar specificity for the gastrin receptors in the gastrointestinal tract (Bock et al., J. Med. Chem., 32, 16–23 (1989); Reyfeld et al., Am. J. Physiol., 240, G255–266 (1981); Beinfeld et al., Neuropeptides, 3, 411–427 (1983)).

The compounds of formula (I) are of low toxicity. Their $LD_{50}$ is generally greater than 40 mg/kg cutaneously in mice.

Among the compounds of formula (I), those are preferred for which R represents phenyl optionally substituted with one or more substituents chosen from halogen atoms and alkyl, alkoxy, hydroxyl, nitro, amino, monoalkylamino, dialkylamino, alkoxycarbonyl, —CO—$NR_8R_9$, —NH—CO—$CH_3$, trifluoromethyl and trifluoromethoxy radicals, $R_1$ represents a hydrogen atom, $R_2$ represents a chain —$(CH_2)_n$—CO—$R_{10}$, $R_3$ represents a hydrogen atom, $R_4$ represents a hydrogen atom, $R_5$ represents a phenylamino radical in which the phenyl ring is optionally substituted by one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH=CH—COOX, —CO—COOX, -alk-$SO_3H$ (in salt form), —CH=CH-alk', —C(=NOH)—COOX, —S-alk-COOX, —SO-alk-COOX, —$S_2$-alk-COOX, —O—$CH_2$-alk'-COOX, —CX=N—O-alk-COOX, -alk-N(OH)—CO-alk, -alk-$SO_2H$, —$SO_2$—NH—CO—$R_{14}$, —$SO_2$—$R_{14}$, —CO—NH—CO—$R_{14}$, —CO—NH—$SO_2$—$R_{14}$, —B(OH)$_2$, —C(NH$_2$)=NOH, —$SO_2$—NH—$R_{15}$, —CO—NH—$R_{15}$,

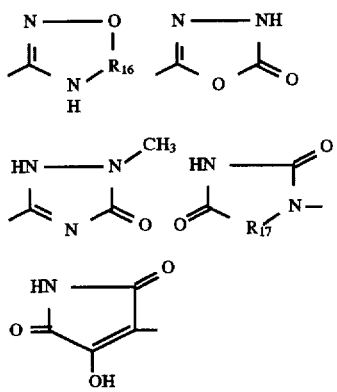

and 2,2-dimethyl-4,6-dioxo-1,3-dioxan-5-yl radicals, $R_6$ represents a hydrogen atom, $R_7$ represents an alkylsulphonyl radical, a radical —$SO_2$—$NR_8R_9$ or a phenylsulphonyl radical in which the phenyl ring is substituted with one or more substituents chosen from halogen atoms and alkyl, alkoxy, hydroxyl, nitro, amino, monoalkylamino, dialkylamino, acylamino, trifluoromethyl and trifluoromethoxy radicals, $R_8$ represents a hydrogen atom or an alkyl or phenylalkyl radical or a phenyl radical which is optionally substituted with one or more substituents chosen from halogen atoms and alkyl, alkoxy and alkylthio radicals, $R_9$ represents an alkyl or phenylalkyl radical or a phenyl radical which is optionally substituted with one or more substituents chosen from halogen atoms and alkyl, alkoxy and alkylthio radicals, or alternatively $R_8$ and $R_9$ form, together with the nitrogen atom to which they are attached, a saturated or unsaturated mono- or polycyclic heterocycle containing 4 to 9 carbon atoms and one or more hetero atoms (O, N) and optionally substituted with one or more alkyl radicals, $R_{10}$ represents a hydroxyl or alkoxy radical, $R_{14}$ represents an alkyl, cycloalkyl or trifluoromethyl radical or a phenyl radical which is optionally substituted with one or more substituents chosen from cyano, alkoxy, nitro and amino radicals and halogen atoms, $R_{15}$ represents a 5-tetrazolyl radical, $R_{16}$ represents C=O or S=O, $R_{17}$ represents O or C=O, n is equal to 0, 1 or 2, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical, the racemic mixtures thereof, the enantiomers thereof and the salts thereof.

The preferred compounds are as follows: (2RS,4SR,5RS)-3-(3-{2-[2-tert-butoxycarbonyl-5-(2-fluorophenyl)-4-(4-chlorophenyl)sulphonyl-1-pyrrolidinyl]-2-oxoethyl}ureido) phenylacetic acid, (2RS,4SR,5RS)-3-(3-{2-[2-tert-butoxycarbonyl-5-(2-fluorophenyl)- 4-(2-fluorophenyl) sulphonyl-1-pyrrolidinyl]-2-oxoethyl}ureido)benzoic acid, (2RS,4SR,5RS)-3-(3-{2-[2-tert-butoxycarbonyl-5-(2-fluorophenyl)-4(3-methoxyphenyl)sulphonyl-1-pyrrolidinyl]-2-oxoethyl}ureido)benzoic acid, (2RS,4SR, 5RS)-3-(3-{2-[2-tert-butoxycarbonyl-5-(2-fluorophenyl)-4-(4-methylphenyl)sulphonyl-1-pyrrolidinyl]-2-oxoethyl}ureido)benzoic acid, (2RS,4SR,5RS)-3-(3-{2-[2-tert-butoxycarbonyl-5-(2-fluorophenyl)-4-(4-nitrophenyl) sulphonyl-1-pyrrolidinyl]-2-oxoethyl}ureido)benzoic acid, (2RS,4SR,5RS)-3-(3-{2-[4-(4-aminophenyl)sulphonyl-2-tert-butoxycarbonyl-5-(2-fluorophenyl)-1-pyrrolidinyl]-2-oxoethyl}ureido)benzoic acid, (2RS,4SR,5RS)-3-(3-{2-[4-(4-acetamidophenyl)sulphonyl-2-tert-butoxycarbonyl-5-(2-fluorophenyl)-1-pyrrolidinyl]-2-oxoethyl}ureido)benzoic acid, (2RS,4SR,5RS)-3-(3-{2-[2-tert-butoxycarbonyl-4-(4-dimethylaminophenyl)sulphonyl-5-(2-fluorophenyl)-1-pyrrolidinyl]-2-oxoethyl}ureido)benzoic acid, (2RS,4SR, 5RS)-3-(3-{2-[2-tert-butoxycarbonyl-5-(2-fluorophenyl)-4-methylsulphonyl-1-pyrrolidinyl]-2-oxoethyl}ureido) benzoic acid, (2RS,4SR,5RS)-3-(3-{2-[4-(4-chlorophenyl) sulphonyl-5-(2-fluorophenyl)-2-isobutylcarbamoyl-1-pyrrolidinyl]-2-oxoethyl}ureido)phenylacetic acid, (2RS, 4SR,5RS)-3-(3-{2-[5-(2-fluorophenyl)-4-(2-fluorophenyl) sulphonyl-2-isobutylcarbamoyl- 1-pyrrolidinyl]-2-oxoethyl}ureido)benzoic acid, (2RS,4SR,5RS)-3-(3-{2-[5-(2-fluorophenyl)-2-isobutylcarbamoyl-4-(3-methoxyphenyl)sulphonyl-1-pyrrolidinyl]-2-oxoethyl}ureido)benzoic acid, (2RS,4SR,5RS)-3-(3-{2-[5-(2-fluorophenyl)-2-isobutylcarbamoyl-4-(4-methylphenyl) sulphonyl-1-pyrrolidinyl]-2-oxoethyl}ureido)benzoic acid, (2RS,4SR,5RS)-3-(3-{2-[5-(2-fluorophenyl)-2-isobutylcarbamoyl-4-(4-nitrophenyl)sulphonyl-1-pyrrolidinyl]-2-oxoethyl}ureido)benzoic acid, (2RS,4SR, 5RS)-3-(3-{2-[4-(4-aminophenyl)sulphonyl-5-(2-fluorophenyl)-2-isobutylcarbamoyl-1-pyrrolidinyl]-2-oxoethyl}ureido)phenylacetic acid, (2RS,4SR,5RS)-3-(3-{2-[4-(4-acetamidophenyl)sulphonyl-5-(2-fluorophenyl)-2-isobutylcarbamoyl-1-pyrrolidinyl]-2-oxoethyl}ureido) benzoic acid, (2RS,4SR,5RS)-3-(3-{2-[2-tert-butoxycarbonyl-5-(2-fluorophenyl)-4-morpholinosulphonyl-1-pyrrolidinyl]-2-oxoethyl}ureido) benzoic acid, and the salts thereof.

The examples which follow illustrate the invention.

EXAMPLE 1

A To a solution of 2.5 g of tert-butyl (2RS,4SR,5RS)-1-{2-[3-(3-methoxycarbonylmethylphenyl)ureido]acetyl}-5-(2-fluorophenyl)-4-(4-chlorophenyl)sulphonyl-2-pyrrolidinecarboxylate in 60 cm$^3$ of methanol and 30 cm$^3$ of distilled water is added, at a temperature in the region of 20° C., 0.2 g of potassium hydroxide. The reaction mixture is stirred for twenty hours at a temperature in the region of 20° C., and then concentrated under reduced pressure. The residue is taken up in 100 cm$^3$ of distilled water, washed with three times 75 cm$^3$ of diethyl ether, acidified to a pH in the region of 1 by aqueous normal hydrochloric acid and extracted with three times 75 cm$^3$ of ethyl acetate. The extracts are combined, washed with three times 50 cm$^3$ of saturated aqueous sodium chloride solution, dried over magnesium sulphate and concentrated under reduced pressure. The residue is purified by chromatography on 80 g of silica contained in a column 3.2 cm in diameter [eluent: dichloromethane/methanol (95/5 by volume)]. The fractions containing the expected product are combined and concentrated under reduced pressure. 0.95 g of (2RS,4SR,5RS)-3-(3-{2-[2-tert-butoxycarbonyl-5-(2-fluorophenyl)-4-(4-chlorophenyl)sulphonyl-1-pyrrolidinyl]-2-oxoethyl}ureido) phenylacetic acid is thus obtained [Rf=0.5; eluent: methylene chloride/methanol (90/10); $^1$H NMR spectrum (250 MHz, (CH$_3$)$_2$SO with addition of a few drops of CD$_3$COOD, at a temperature of 393 K, δ in ppm): 1.54 (s, 9H: C(CH$_3$)$_3$); from 2.40 to 2.60 and 2.85 (2 mts, 1H each: CH$_2$ at 3); 3.50 (s, 2H: ArCH$_2$COO); 3.70 and 3.97 (broad d and d respectively, J=17 Hz, 1H each: COCH$_2$N); 4.09 (mt, 1H: H4); 4.68 (t, J=8 Hz, 1H: H2); 5.73 (d, J=3 Hz, 1H: H5); 6.86 (broad d, J=7.5 Hz, 1H: aromatic H (H4: ortho to the CH$_2$)); from 7.00 to 7.40 (mt, 6H: aromatic H); 7.68 (broad d, J=8.5 Hz, 2H: H of the aromatic at 4 (H ortho to the Cl)); 7.82 (broad t, J=8 Hz, 1H: H of the aromatic at 5 (H6)); 7.96 (broad d, J=8.5 Hz, 2H: aromatic H at 4 (H meta to the Cl))].

B tert-Butyl (2RS,4SR,5RS)-1-{2-[3-(3-methoxycarbonylmethylphenyl)ureido]acetyl}-5-(2-fluorophenyl)-4-(4-chlorophenyl)sulphonyl-2-pyrrolidinecarboxylate may be prepared in the following way: to a solution of 2.4 g of tert-butyl (2RS,4SR,5RS)-5-(2-fluorophenyl)-4-(4-chlorophenyl)sulphonyl-2-pyrrolidinecarboxylate hydrochloride in 100 cm$^3$ of dichloromethane is added 0.7 cm$^3$ of triethylamine. The mixture is washed with three times 50 cm$^3$ of distilled water and the organic phase dried over magnesium sulphate. The residue is dissolved in 75 cm$^3$ of acetonitrile. 1.35 g of 2-[3-(3-methoxycarbonylmethylphenyl)ureido]acetic acid are then added, followed by 1.1 g of N,N'-dicyclohexylcarbodiimide. The reaction mixture is stirred for twenty hours at a temperature in the region of 20° C. The reaction mixture is concentrated under reduced pressure, taken up in 50 cm$^3$ of ethyl acetate, filtered, rinsed with twice 25 cm$^3$ of ethyl acetate and concentrated under reduced pressure. The residue is purified by chromatography on 120 g of silica contained in a column 3.2 cm in diameter [eluent: cyclohexane/ethyl acetate (50/50 by volume)]. The fractions containing the expected product are combined and concentrated under reduced pressure. 3 g of tert-butyl (2RS,4SR, 5RS)-1-{2-[3-(3-methoxycarbonylmethylphenyl)ureido] acetyl}-5-(2-fluorophenyl)-4-(4-chlorophenyl)sulphonyl-2-pyrrolidinecarboxylate are thus obtained in the form of a foam, which is used without further purification in the subsequent syntheses.

C tert-Butyl (2RS,4SR,5RS)-5-(2-fluorophenyl)-4-(4-chlorophenyl)sulphonyl-2-pyrrolidinecarboxylate hydrochloride may be prepared in the following way: to a solution of 7.2 g of tert-butyl (2-fluorobenzylideneamino)acetate in 200 cm$^3$ of acetonitrile are successively added 6.1 g of 4-chlorophenyl vinyl sulphone, 7.52 g of silver acetate and 5.1 cm$^3$ of triethylamine. The reaction mixture is stirred for four hours at a temperature in the region of 20° C., and then poured into 200 cm$^3$ of saturated aqueous ammonium chloride solution. The suspension is filtered, the precipitate is washed with twice 50 cm$^3$ of distilled water and the filtrate is extracted with three times 100 cm$^3$ of ethyl acetate. The extracts are combined, washed with twice 100 cm$^3$ of distilled water, dried over magnesium sulphate and concentrated under reduced pressure. The residue is purified by chromatography on 150 g of silica contained in a column 4.2 cm in diameter [eluent: cyclohexane/ethyl acetate (70/30 by volume)]. The fractions containing the expected product are combined and concentrated under reduced pressure. The residue is dissolved in 20 cm$^3$ of ethyl acetate and treated with 20 cm$^3$ of aqueous normal hydrochloric acid solution. The precipitate which forms is filtered and washed successively with water and with ethyl acetate. 4 g of tert-butyl (2RS,4SR,5RS)-5-(2-fluorophenyl)-4-(4-chlorophenyl) sulphonyl-2-pyrrolidinecarboxylate hydrochloride are thus obtained, melting at 138° C. Starting with other fractions, and after recrystallization from acetonitrile, 3 g of tert-butyl (2RS,4RS,5RS)-5-(2-fluorophenyl)-4-(4-chlorophenyl) sulphonyl-2-pyrrolidinecarboxylate are also obtained, melting at 174° C.

D tert-Butyl (2-fluorobenzylideneamino)acetate may be prepared in the following way: to a suspension of 3 g of 4 Å molecular sieves in a solution containing 5.01 g of tert-butyl glycinate hydrochloride and 3.15 cm$^3$ of 2-fluorobenzaldehyde in 45 cm$^3$ of dichloromethane are added dropwise 4.2 cm$^3$ of triethylamine at a temperature in the region of 20° C. The reaction mixture is stirred for seventy-two hours at a temperature in the region of 20° C. and concentrated under reduced pressure. The residue is taken up in 50 cm$^3$ of diethyl ether and filtered, and the precipitate is rinsed with twice 25 cm$^3$ of diethyl ether. The filtrate is concentrated under reduced pressure. 7.2 g of tert-butyl (2-fluorobenzylideneamino)acetate are thus obtained in the form of an oil, which is used without further purification in the subsequent syntheses.

E 4-Chlorophenyl vinyl sulphone may be prepared in the following way: to a solution of 18.5 g of 2-chloroethyl 4-chlorophenyl sulphone in 100 cm$^3$ of tetrahydrofuran is added over five minutes, at a temperature in the region of 30° C., a solution of 16.3 cm$^3$ of triethylamine in 50 cm$^3$ of tetrahydrofuran. The reaction mixture is stirred for twenty hours at a temperature in the region of 20° C. The suspension is filtered and the precipitate rinsed with three times 25 cm$^3$ of tetrahydrofuran. The filtrate is concentrated under reduced pressure. 16 g of 4-chlorophenyl vinyl sulphone are thus obtained in the form of a yellow oil, which is used without further purification in the subsequent syntheses.

F 2-Chloroethyl 4-chlorophenyl sulphone may be prepared in the following way: to a solution of 18 g of 2-chloroethyl 4-chlorophenyl sulphide in 87 cm$^3$ of acetic acid is added over thirty minutes, at a temperature in the region of 48° C., a mixture of 24.8 cm$^3$ of aqueous 30% hydrogen peroxide solution and 40 cm$^3$ of acetic acid. The reaction medium is stirred for four hours at a temperature in the region of 70° C., then for eight hours at a temperature in the region of 90° C. and then for twenty hours at a temperature in the region of 20° C. 200 cm$^3$ of distilled water are then added and the reaction medium is filtered. The precipitate is washed with five times 75 cm$^3$ of distilled water and dried under reduced pressure at a temperature in the region of 40° C. 18.5 g of 2-chloroethyl 4-chlorophenyl sulphone are thus obtained, melting at 91° C.

G 2-Chloroethyl 4-chlorophenyl sulphide may be prepared in the following way: to a solution of 14.5 g of 4-chlorothiophenol and 0.24 cm$^3$ of aliquat in 114 cm$^3$ of 1,2-dichloroethane is added over two hours, at a temperature in the region of 20° C., a solution of 4.94 g of sodium hydroxide in 62 cm$^3$ of distilled water. The reaction medium is stirred for twenty hours at a temperature in the region of 20° C. and the phases are then allowed to separate out after settling has taken place. The organic phase is washed with 60 cm$^3$ of aqueous 0.1N hydrochloric acid solution and then with twice 50 cm$^3$ of saturated aqueous sodium chloride solution, dried over magnesium sulphate and concentrated under reduced pressure. The residue is purified by chromatography on 200 g of silica contained in a column 6 cm in diameter (eluent: cyclohexane). The fractions containing the expected product are combined and concentrated under reduced pressure. 18 g of 2-chloroethyl 4-chlorophenyl sulphide are thus obtained in the form of a colourless oil, which is used without further purification in the subsequent syntheses.

H 2-[3-(3-Methoxycarbonylmethylphenyl)ureido]acetic acid may be prepared in the following way: to a solution of 9.42 g of glycine and 34.69 g of potassium carbonate in 220 cm$^3$ of water is added, at a temperature in the region of 5° C., a solution of 24 g of methyl 3-isocyanatophenylacetate in 170 cm$^3$ of 1,4-dioxane. The reaction mixture is stirred for twenty hours at a temperature in the region of 20° C. and then acidified to a pH in the region of 1 with aqueous 4N hydrochloric acid solution. The insoluble product is isolated by filtration, washed with three times 50 cm$^3$ of water and air-dried. After recrystallization from ethyl acetate, 46.85 g of 2-[3-(3-methoxycarbonylmethylphenyl)ureido]acetic acid are thus obtained, melting at 136° C.

I Methyl 3-isocyanatophenylacetate may be prepared in the following way: to a suspension of 1 g of charcoal and 6 cm$^3$ of trichloromethyl chloroformate in 70 cm$^3$ of toluene are added, at a temperature in the region of –20° C. and under argon, 8.25 g of methyl 3-aminophenylacetate dissolved in 100 cm$^3$ of toluene. The reaction mixture is stirred and maintained at a temperature in the region of –20° C. for fifteen minutes followed, after returning to a temperature in the region of 20° C., by heating at reflux for two hours thirty minutes. The mixture is then degassed by sparging with argon for thirty minutes, filtered over Celite, rinsed with 50 cm$^3$ of dichloromethane and concentrated under reduced pressure at a temperature in the region of 50° C. 9.30 g of methyl 3-isocyanatophenylacetate are thus obtained in the form of an oil, which is used without further purification in the subsequent syntheses.

Methyl 3-aminophenylacetate may be prepared according to the method described by W. A. Jacobs et al., J. Amer. Chem. Soc., 34, 2420 (1917).

EXAMPLE 2

A To a solution of 4.1 g of tert-butyl (2RS,4SR,5RS)-1-{2-[3-(3-benzyloxycarbonylphenyl)ureido]acetyl}-5-(2-fluorophenyl)-4-(2-fluorophenyl)sulphonyl-2-pyrrolidinecarboxylate in 100 cm$^3$ of ethanol is added 0.4 g of 10% palladium-on-charcoal. The suspension is stirred for twenty hours at a temperature in the region of 20° C. under a hydrogen atmosphere (130 kPa). The catalyst is separated out by filtration on Celite and the filtrate is concentrated to dryness under reduced pressure. The residue is taken up in an isopropyl acetate/diisopropyl ether mixture (10/90 by volume) and filtered, and the precipitate is rinsed with an isopropyl acetate/diisopropyl ether mixture (10/90 by volume) and then with diisopropyl ether, and dried under reduced pressure at a temperature in the region of 40° C. 3 g of (2RS,4SR,5RS)-3-(3-{2-[2-tert-butoxycarbonyl-5-(2-(2-fluorophenyl)-4-(2-fluorophenyl)sulphonyl-1-pyrrolidinyl]-2-oxoethyl}ureido)benzoic acid are thus obtained [Rf=0.3; eluent: methylene chloride/methanol (90/10); $^1$H NMR spectrum (20 MHz, (CD$_3$)$_2$SO with addition of a few drops of CD$_3$COOD, at a temperature of 383 K, δ in ppm): 1.55 (s, 9H: C(CH$_3$)$_3$); from 2.45 to 2.65 and 2.88 (2 mts, 1H each: CH$_2$ at 3); 3.75 and 4.00 (broad d and d respectively, J=17 Hz, 1H each: COCH$_2$N); 4.15 (mt, 1H:

H4); 4.76 (t, J=8 Hz, 1H: H2); 5.73 (d, J=3.5 Hz, 1H: H5); from 6.95 to 8.05 (mt, 12H: aromatic H)].

B tert-Butyl (2RS,4SR,5RS)-1-{2-[3-(3-benzyloxycarbonylphenyl)ureido]acetyl}-5-(2-fluorophenyl)-4-(2-fluorophenyl)sulphonyl-2-pyrrolidinecarboxylate may be prepared as described in Example 1B but starting with 3 g of tert-butyl (2RS,4SR,5RS)-5-(2-fluorophenyl)-4-(2-fluorophenyl)sulphonyl-2-pyrrolidinecarboxylate, 2.33 g of 2-[3-(3-benzyloxycarbonylphenyl)ureido]acetic acid and 1.46 g of N,N'-dicyclohexylcarbodiimide in 75 cm³ of acetonitrile. After treatment, 4.1 g of tert-butyl (2RS,4SR,5RS)-1-{2-[3-(3-benzyloxycarbonylphenyl)ureido]acetyl}-5-(2-fluorophenyl)-4-(2-fluorophenyl)sulphonyl-2-pyrrolidinecarboxylate are obtained in the form of a foam, which is used without further purification in the subsequent syntheses.

C tert-Butyl (2RS,4SR,5RS)-5-(2-fluorophenyl)-4-(2-fluorophenyl)sulphonyl-2-pyrrolidinecarboxylate may be prepared as described in Example 1C, but starting with 4.75 g of tert-butyl (2-fluorobenzylideneamino)acetate, 3.73 g of 2-fluorophenyl vinyl sulphone, 5 g of silver acetate and 3.4 cm³ of triethylamine in 200 cm³ of acetonitrile. After treatment, 3 g of tert-butyl (2RS,4SR,5RS)-5-(2-fluorophenyl)-4-(2-fluorophenyl)sulphonyl-2-pyrrolidinecarboxylate melting at 126° C. and 2.55 g of tert-butyl (2RS,4RS,5RS)-5-(2-fluorophenyl)-4-(2-fluorophenyl)sulphonyl-2-pyrrolidinecarboxylate melting at 202° C. are obtained.

D 2-Fluorophenyl vinyl sulphone may be prepared as described in Example 1E, but starting with 11.5 g of 2-chloroethyl 2-fluorophenyl sulphone, 10.6 cm³ of triethylamine and 150 cm³ of tetrahydrofuran. After treatment, 9 g of 2-fluorophenyl vinyl sulphone are obtained in the form of a yellow oil, which is used without further purification in the subsequent syntheses.

E 2-Chloroethyl 2-fluorophenyl sulphone may be prepared as described in Example 1F, but starting with 10 g of 2-chloroethyl 2-fluorophenyl sulphide, 14.3 cm³ of aqueous 30% hydrogen peroxide solution and 75 cm³ of acetic acid. After treatment, 11.5 g of 2-chloroethyl 2-fluorophenyl sulphone are obtained in the form of an orange-coloured oil, which is used without further purification in the subsequent syntheses.

F 2-Chloroethyl 2-fluorophenyl sulphide may be prepared as described in Example 1G, but starting with 6.4 g of 2-fluorothiophenol, 0.12 cm³ of aliquat, 2.47 g of sodium hydroxide, 31 cm³ of distilled water and 57 cm³ of 1,2-dichloroethane. After treatment, 10 g of 2-chloroethyl 2-fluorophenyl sulphide are obtained in the form of a yellow oil, which is used without further purification in the subsequent syntheses.

G 2-[3-(3-Benzyloxycarbonylphenyl)ureido]acetic acid may be prepared as described in Example 1H, but starting with 36.7 g of benzyl 3-isocyanatobenzoate, 10.9 g of glycine and 40.1 g of potassium carbonate in a mixture of 245 cm³ of distilled water and 195 cm³ of 1,4-dioxane. After treatment, 38.5 g of 2-[3-(3-benzyloxycarbonylphenyl) ureido]acetic acid are obtained, melting at 168° C.

H Benzyl 3-isocyanatobenzoate may be prepared as described in Example 1I, but starting with 33 g of benzyl 3-aminobenzoate, 2.9 g of charcoal and 28.7 g of bis (trichloromethyl)carbonate in 500 cm³ of toluene. After treatment, 38 g of benzyl 3-isocyanatobenzoate are obtained in the form of an oil, which is used without further purification in the subsequent syntheses.

Benzyl 3-aminobenzoate may be prepared according to the method described by H. Bredereck Ber., 91, 215 (1948).

EXAMPLE 3

A The process is performed as described in Example 2A, but starting with 5.3 g of tert-butyl (2RS,4SR,5RS)-1-{2-[3-(3-benzyloxycarbonylphenyl)ureido]acetyl}-5-(2-fluorophenyl)-4-(3-methoxyphenyl)sulphonyl-2-pyrrolidinecarboxylate, 0.4 g of 10% palladium-on-charcoal and 100 cm³ of ethanol under a hydrogen atmosphere (130 kPa). After treatment, 3.5 g of (2RS,4SR,5RS)-3-(3-{2-[2-tert-butoxycarbonyl-5-(2-fluorophenyl)-4-(3-methoxyphenyl)sulphonyl-1-pyrrolidinyl]-2-oxoethyl}ureido)benzoic acid are obtained [Rf=0.3; eluent: methylene chloride/methanol (90/10); ¹H NMR spectrum (250 MHz, (CD₃)₂SO with addition of a few drops of CD₃COOD, at a temperature of 393 K, δ in ppm): 1.54 (s, 9H: C(CH₃)₃); from 2.40 to 2.60 and 2.82 (2 mts, 1H each: CH₂ at 3); 3.68 and 3.98 (broad d and d respectively, J=17 Hz, 1H each: COCH₂N); 3.88 (s, 3H: OCH₃); 4.11 (mt, 1H: H4); 4.67 (t, J=8 Hz, 1H: H2); 5.72 (d, J=3 Hz, 1H: H5); from 7.00 to 7.65 (mt, 10H: aromatic H); 7.80 (broad t, J=8 Hz, 1H: H of the aromatic at 5 (H6)); 8.00 (mt, 1H: aromatic H (H2: ortho to the COOH))].

B tert-Butyl (2RS,4SR,5RS)-1-{2-[3-(3-benzyloxycarbonylphenyl)ureido]acetyl}-5-(2-fluorophenyl)-4-(3-methoxyphenyl)sulphonyl-2-pyrrolidinecarboxylate may be prepared as described in Example 1B, but starting with 3.7 g of tert-butyl (2RS,4SR,5RS)-5-(2-fluorophenyl)-4-(3-methoxyphenyl)sulphonyl-2-pyrrolidinecarboxylate, 2.73 g of 2-[3-(3-benzyloxycarbonylphenyl)ureido]acetic acid and 1.75 g of N,N'-dicyclohexylcarbodiimide in 75 cm³ of acetonitrile. After treatment, 4.3 g of tert-butyl (2RS,4SR,5RS)-1-{2-[3-(3-benzyloxycarbonylphenyl)ureido]acetyl}-5-(2-fluorophenyl)-4-(3-methoxyphenyl)sulphonyl-2-pyrrolidinecarboxylate are obtained in the form of a foam, which is used without further purification in the subsequent syntheses.

C tert-Butyl (2RS,4SR,5RS)-5-(2-fluorophenyl)-4-(3-methoxyphenyl)sulphonyl-2-pyrrolidinecarboxylate may be prepared as described in Example 1C, but starting with 4.75 g of tert-butyl (2-fluorobenzylideneamino)acetate, 3.73 g of 3-methoxyphenyl vinyl sulphone, 5 g of silver acetate and 3.4 cm³ of triethylamine in 200 cm³ of acetonitrile. After treatment, 3.9 g of tert-butyl (2RS,4SR,5RS)-5-(2-fluorophenyl)-4-(3-methoxyphenyl)sulphonyl-2-pyrrolidinecarboxylate in the form of an orange-coloured oil, which is used without further purification in the subsequent syntheses, and 1.1 g of tert-butyl (2RS,4RS,5RS)-5-(2-fluorophenyl)-4-(3-methoxyphenyl)sulphonyl-2-pyrrolidinecarboxylate melting at 140° C. are obtained.

D 3-Methoxyphenyl vinyl sulphone may be prepared as described in Example 1E, but starting with 11.8 g of 2-chloroethyl 3-methoxyphenyl sulphone, 10.6 cm³ of triethylamine and 150 cm³ of tetrahydrofuran. After treatment, 9 g of 3-methoxyphenyl vinyl sulphone are obtained in the form of a yellow oil, which is used without further purification in the subsequent syntheses.

E 2-Chloroethyl 3-methoxyphenyl sulphone may be prepared as described in Example 1F, but starting with 10.5 g of 2-chloroethyl 3-methoxyphenyl sulphide, 14.3 cm³ of aqueous 30% hydrogen peroxide solution and 75 cm³ of acetic acid. After treatment, 11.8 g of 2-chloroethyl 3-methoxyphenyl sulphone are obtained in the form of an orange-coloured oil, which is used without further purification in the subsequent syntheses.

F 2-Chloroethyl 3-methoxyphenyl sulphide may be prepared as described in Example 1G, but starting with 7 g of 3-methoxythiophenol, 0.12 cm$^3$ of aliquat, 2.47 g of sodium hydroxide, 31 cm$^3$ of distilled water and 57 cm$^3$ of 1,2-dichloroethane. After treatment, 10.5 g of 2-chloroethyl 3-methoxyphenyl sulphide are obtained in the form of a yellow oil, which is used without further purification in the subsequent syntheses.

EXAMPLE 4

A The process is performed as described in Example 1A, but starting with 2.2 g of tert-butyl (2RS,4SR,5RS)-5-(2-fluorophenyl)-1-{2-[3-(3-methoxycarbonylphenyl)ureido]acetyl}-4-(4-methylphenyl)sulphonyl-2-pyrrolidinecarboxylate and 0.19 g of potassium hydroxide in a mixture of 60 cm$^3$ of methanol and 20 cm$^3$ of distilled water. After treatment, 0.27 g of (2RS,4SR,5RS)-3-(3-{2-[2-tert-butoxycarbonyl-5-(2-fluorophenyl)-4-(4-methylphenyl)sulphonyl-1-pyrrolidinyl]-2-oxoethyl}ureido)benzoic acid is obtained [Rf=0.5; eluent: methylene chloride/methanol (90/10); $^1$H NMR spectrum (200 MHz, (CD$_3$)$_2$SO with addition of a few drops of CD$_3$COOD at a temperature of 373 K, δ in ppm): 1.52 (s, 9H): C(CH$_3$)$_3$); from 2.35 to 2.55 and 2.79 (2 mts, 1H each: CH$_2$ at 3); 2.45 (s, 3H: ArCH$_3$); 3.66 and 3.96 (broad d and d respectively, J=17 Hz, 1H each: COCH$_2$N); 4.05 (mt, 1H: H4); 4.62 (t, J=8 Hz, 1H: H2); 5.70 (d, J=3 Hz, 1H: H5); from 7.00 to 7.55 (mt, 8H: aromatic H); 7.80 (mt, 1H: H of the aromatic at 5 (H6)); 7.85 (d, J=8 Hz, 2H: H of the aromatic at 4 (ortho to the CH$_3$)); 8.00 Ct, J=1.5 Hz, 1H: aromatic H CH2: ortho to the COOH))].

B tert-Butyl (2RS,4SR,5RS)-5-(2-fluorophenyl)-1-{2-[3-(3-methoxycarbonylphenyl)ureido]acetyl}-4-(4-methylphenyl)sulphonyl-2-pyrrolidinecarboxylate may be prepared as described in Example 1B, but starting with 2.1 g of tert-butyl (2RS,4SR,5RS)-5-(2-fluorophenyl)-4-(4-methylphenyl)sulphonyl-2-pyrrolidinecarboxylate, 1.26 g of 2-[3-(3-methoxycarbonylphenyl)ureido]acetic acid and 1.1 g of N,N'-dicyclohexylcarbodiimide in 100 cm$^3$ of acetonitrile. After treatment, 2.2 g of tert-butyl (2RS,4SR,5RS)-5-(2-fluorophenyl)-1-{2-[3-(3-methoxycarbonylphenyl)ureido]acetyl}-4-(4-methylphenyl)sulphonyl-2-pyrrolidinecarboxylate are obtained in the form of a foam, which is used without further purification in the subsequent syntheses.

C tert-Butyl (2RS,4SR,5RS)-5-(2-fluorophenyl)-4-(4-methylphenyl)sulphonyl-2-pyrrolidinecarboxylate may be prepared as described in Example 1C, but starting with 4.75 g of tert-butyl (2-fluorobenzylideneamino)acetate, 3.65 g of 4-methylphenyl vinyl sulphone, 5 g of silver acetate and 3.65 cm$^3$ of triethylamine in 150 cm$^3$ of acetonitrile. After treatment, 4 g of tert-butyl (2RS,4SR,5RS)-5-(2-fluorophenyl)-4-(4-methylphenyl)sulphonyl-2-pyrrolidinecarboxylate in the form of an orange-coloured oil, which is used without further purification in the subsequent syntheses and 1.1 g of tert-butyl (2RS,4RS,5RS)-5-(2-fluorophenyl)-4-(4-methylphenyl)sulphonyl-2-pyrrolidinecarboxylate melting at 146° C. are obtained.

D 4-Methylphenyl vinyl sulphone may be prepared as described in Example 1E, but starting with 21 g of 2-chloroethyl 4-methylphenyl sulphone, 20.2 cm$^3$ of triethylamine and 250 cm$^3$ of tetrahydrofuran. After treatment, 13.2 g of 4-methylphenyl vinyl sulphone are obtained, melting at 66° C.

E 2-Chloroethyl 4-methylphenyl sulphone may be prepared as described in Example 1F, but starting with 13 g of 2-chloroethyl 4-methylphenyl sulphide, 28.6 cm$^3$ of aqueous 30% hydrogen peroxide solution and 150 cm$^3$ of acetic acid. After treatment, 21 g of 2-chloroethyl 4-methylphenyl sulphone are obtained in the form of an orange-coloured oil, which is used without further purification in the subsequent syntheses.

F 2-Chloroethyl 4-methylphenyl sulphide may be prepared as described in Example 1G, but starting with 12.42 g of 4-methylthiophenol, 0.24 cm$^3$ of aliquat, 4.94 g of sodium hydroxide, 62 cm$^3$ of distilled water and 114 cm$^3$ of 1,2-dichloroethane. After treatment, 19 g of 2-chloroethyl 4-methylphenyl sulphide are obtained in the form of a yellow oil, which is used without further purification in the subsequent syntheses.

G 2-[3-(3-Methoxycarbonylphenyl)ureido]acetic acid may be prepared as described in Example 1H, but starting with 5.88 g of methyl 3-isocyanatobenzoate, 2.5 g of glycine and 9.2 g of potassium carbonate in a mixture of 90 cm$^3$ of distilled water and 75 cm$^3$ of 1,4-dioxane. After treatment, 5.27 g of 2-[3-(3-methoxycarbonylphenyl)ureido]acetic acid are obtained, melting at 220° C.

EXAMPLE 5

A The process is performed as described in Example 1A, but starting with 2.9 g of tert-butyl (2RS,4SR,5RS)-5-(2-fluorophenyl)-1-{2-[3-(3-methoxycarbonylphenyl)ureido]acetyl}-4-(4-nitrophenyl)sulphonyl-2-pyrrolidinecarboxylate and 0.24 g of potassium hydroxide in a mixture of 60 cm$^3$ of methanol and 20 cm$^3$ of distilled water. After treatment, 0.25 g of (2RS,4SR,4RS)-3-(3-{2-[2-tert-butoxycarbonyl-5-(2-fluorophenyl)-4-(4-nitrophenyl)sulphonyl-1-pyrrolidinyl]-2-oxoethyl}ureido) benzoic acid is obtained [Rf=0.3; eluent: methylene chloride/methanol (90/10); $^1$H NMR spectrum (200 MHz, (CD$_3$)$_2$SO with addition of a few drops of CD$_3$COOD, at a temperature of 393 K, δ in ppm): 1.55 (s, 9H: C(CH$_3$)$_3$); from 2.40 to 2.60 and 2.88 (2 mts, 1H each: CH$_2$ at 3); 3.71 and 4.02 (broad d and d respectively, J=17 Hz, 1H each: COCH$_2$N); 4.28 (mt, 1H: H4); 4.72 (t, J=8 Hz, 1H: H$_2$); 5.76 (d, J=3.5 Hz, 1H: H5); from 6.95 to 7.65 (mt, 6H: aromatic H); 7.81 (mt, 1H: H of the aromatic at 5 (H6)); 8.00 (t, J=1.5 Hz, 1H: aromatic H (H2: ortho to the COOH)); 8.27 and 8.42 (2d, J=8 Hz, 2H each: H of the aromatic at 4)].

B tert-Butyl (2RS,4SR,5RS)-5-(2-fluorophenyl)-1-{2-[3-(3-methoxycarbonylphenyl)ureido]acetyl}-4-(4-nitrophenyl)sulphonyl-2-pyrrolidinecarboxylate may be prepared as described in Example 1B, but starting with 2.25 g of tert-butyl (2RS,4SR,5RS)-5-(2-fluorophenyl)-4-(4-nitrophenyl)sulphonyl-2-pyrrolidinecarboxylate, 1.26 g of 2-[3-(3-methoxycarbonylphenyl)ureido]acetic acid and 1.1 g of N,N'-dicyclohexylcarbodiimide in 100 cm$^3$ of acetonitrile. After treatment, 2.9 g of tert-butyl (2RS,4SR,5RS)-5-(2-fluorophenyl)-1-{2-[3-(3-methoxycarbonylphenyl)ureido]acetyl}-4-(4-nitrophenyl)sulphonyl-2-pyrrolidinecarboxylate are obtained in the form of a foam, which is used without further purification in the subsequent syntheses.

C tert-Butyl (2RS,4SR,5RS)-5-(2-fluorophenyl)-4-(4-nitrophenyl)sulphonyl-4-pyrrolidinecarboxylate may be prepared as described in Example 1C, but starting with 9.5 g of tert-butyl (2-fluorobenzylideneamino)acetate, 8.5 g of 4-nitrophenyl vinyl sulphone, 10 g of silver acetate and 7.3 cm$^3$ of triethylamine in 200 cm$^3$ of acetonitrile. After treatment, 6 g of tert-butyl (2RS,4SR,5RS)-5-(2-fluorophenyl)-4-(4-nitrophenyl)sulphonyl-2-pyrrolidinecarboxylate in the form of an orange-coloured oil, which is used without further purification in the subsequent syntheses, and 5.5 g of tert-butyl (2RS,4RS,5RS)-5-(2-fluorophenyl)-4-(4-nitrophenyl)sulphonyl-2-pyrrolidinecarboxylate melting at 218° C. are obtained.

D 4-Nitrophenyl vinyl sulphone may be prepared as described in Example 1E, but starting with 19 g of 2-chloroethyl 4-nitrophenyl sulphone, 16.1 cm³ of triethylamine and 250 cm³ of tetrahydrofuran. After treatment, 12.7 g of 4-nitrophenyl vinyl sulphone are obtained, melting at 114° C.

E 2-Chloroethyl 4-nitrophenyl sulphone may be prepared as described in Example 1F, but starting with 20 g of 2-chloroethyl 4-nitrophenyl sulphide, 26.4 cm³ of aqueous 30% hydrogen peroxide solution and 150 cm³ of acetic acid. After treatment, 19 g of 2-chloroethyl 4-nitrophenyl sulphone are obtained, melting at 130° C.

F 2-Chloroethyl 4-nitrophenyl sulphide may be prepared as described in Example 1G, but starting with 15.52 g of 4-nitrothiophenol, 0.24 cm³ of aliquat, 4.94 g of sodium hydroxide, 62 cm³ of distilled water and 114 cm³ of 1,2-dichloroethane. After treatment, 20 g of 2-chloroethyl 4-nitrophenyl sulphide are obtained in the form of a yellow solid melting below 50° C.

EXAMPLE 6

A To a solution of 1.7 g of tert-butyl (2RS,4SR,5RS)-1-{2-[3-(3-benzyloxycarbonylphenyl)ureido]acetyl}-5-(2-fluorophenyl)-4-(4-nitrophenyl)sulphonyl-2-pyrrolidinecarboxylate in 100 cm³ of ethanol is added 0.2 g of 10% palladium-on-charcoal. The suspension is stirred for twenty hours at a temperature in the region of 20° C. under a hydrogen atmosphere (130 kPa). The catalyst is separated out by filtration on Celite and the filtrate is concentrated to dryness under reduced pressure. The residue is purified by chromatography on 40 g of silica contained in a column 2.2 cm in diameter [eluent: dichloromethane/methanol (90/10 by volume)]. The fractions containing the expected product are combined and concentrated under reduced pressure. 0.95 g of (2RS,4SR,5RS)-3-(3-{2-[4-(4-aminophenyl)sulphonyl-2-tert-butoxycarbonyl-5-(2-fluorophenyl)-1-pyrrolidinyl]-2-oxoethyl}ureido)benzoic acid is thus obtained [Rf=0.2; eluent: methylene chloride/methanol (90/10); ¹H NMR spectrum (200 MHz, (CD₃)₂SO with addition of a few drops of CD₃COOD, at a temperature of 393 K, δ in ppm): 1.55 (s, 9H: C(CH₃)₃); from 2.30 to 2.55 and 2.76 (2 mts, 1H each: CH₂ at 3); 3.68 and 4.00 (broad d and d respectively, J=17 Hz, 1H each:COCH₂N); 3.84 (mt, 1H: H4); 4.62 (t, J=8 Hz, 1H: H2); 5,72 (d, J=3 Hz, 1H: H5); 6.76 (d, J=8 Hz, 2H: H of the aromatic at 4 (H ortho to the NH₂)); 7.00 to 7.70 (mt, 6H: aromatic H); 7.58 (d, J=8 Hz, 2H: H of the aromatic at 4 (H meta to the NH₂)); 7.82 (broad t, J=8 Hz, 1H: H of the aromatic at 5 (H6)); 8.00 (t, J=1.5 Hz, 1H: aromatic H (H2: ortho to the COOH))].

B tert-Butyl (2RS,4SR,5RS)-1-{2-[3-(3-benzyloxycarbonylphenyl)ureido]acetyl}-5-(2-fluorophenyl)-4-(4-nitrophenyl)sulphonyl-2-pyrrolidinecarboxylate may be prepared as described in Example 1B, but starting with 1.35 g of tert-butyl (2RS,4SR,5RS)-5-(2-fluorophenyl)-4-(4-nitrophenyl)sulphonyl-2-pyrrolidinecarboxylate, 0.99 g of 2-[3-(3-benzyloxycarbonylphenyl)ureido]acetic acid and 0.62 g of N,N'-dicyclohexylcarbodiimide in 50 cm³ of acetonitrile. After treatment, 1.7 g of tert-butyl (2RS,4SR,5RS)-1-{2-[3-(3-benzyloxycarbonylphenyl)ureido]acetyl}-5-(2-fluorophenyl)-4-(4-nitrophenyl)sulphonyl-2-pyrrolidinecarboxylate are obtained in the form of a foam, which is used without further purification in the subsequent syntheses.

EXAMPLE 7A

The process is performed as described in Example 2A, but starting with 1.6 g of tert-butyl (2RS,4SR,5RS)-4-(4-acetamidophenyl)sulphonyl-1-{2-[3-(3-benzyloxycarbonylphenyl)ureido]acetyl}-5-(2-fluorophenyl)-2-pyrrolidinecarboxylate, 0.2 g of 10% palladium-on-charcoal and 100 cm³ of ethanol under a hydrogen atmosphere (130 kPa). After treatment, 0.9 g of (2RS,4SR,5RS)-3-(3-{2-[4-(4-acetamidophenyl)sulphonyl-2-tert-butoxycarbonyl-5-(2-fluorophenyl)-1-pyrrolidinyl]-2-oxoethyl}ureido)benzoic acid is obtained [Rf=0.3; eluent: methylene chloride/methanol (90/10); ¹H NMR spectrum (300 MHz, (CD₃)₂SO, at a temperature of 393 K, δ in ppm): 1.55 (s, 9H: C(CH₃)₃); 2.12 (s, 3H: COCH₃); 2.44 and 2.79 (2 mts, 1H each: CH₂ at 3); 3.68 and 3.99 (mt and dd respectively (J=17 and 4.5 Hz), 1H each: COCH₂N); 4.03 (mt, 1H: H4); 4.65 (broad t, J=7 Hz, 1H: H2); 5,72 (d, J=3 Hz, 1H: H5); 6.20 (t, J=4.5 Hz, 1H: NHCO); from 7.05 to 7.65 (mt, 6H: aromatic H); 7.80 (broad t, J=8 Hz, 1H: H of the aromatic at 5 (H6)); 7.88 (limiting AB, J=7.5 Hz, 4H: H of the aromatic at 4); 8.00 (mt, 1H: aromatic H (H2: ortho to the COOH)); 8.65 (s, 1H: CONHAr); 10.03 (s, 1H: ArNH)].

B tert-Butyl (2RS,4SR,5RS)-4-(4-acetamidophenyl) sulphonyl-1-{2-[3-(3-benzyloxycarbonylphenyl)ureido] acetyl}-5-(2-fluorophenyl)-2-pyrrolidinecarboxylate may be prepared as described in Example 1B, but starting with 1.16 g of tert-butyl (2RS,4SR,5RS)-4-(4-acetamidophenyl) sulphonyl-5-(2-fluorophenyl)-2-pyrrolidinecarboxylate, 0.82 g of 2-[3-(3-benzyloxycarbonylphenyl)ureido]acetic acid and 0.52 g of N,N'-dicyclohexylcarbodiimide in 100 cm³ of acetonitrile. After treatment, 1.6 g of tert-butyl (2RS,4SR,5RS)-4-(4-acetamidophenyl)sulphonyl-1-{2-[3-(3-benzyloxycarbonylphenyl)ureido]acetyl}-5-(2-fluorophenyl)-2-pyrrolidinecarboxylate are obtained in the form of a foam, which is used without further purification in the subsequent syntheses.

C tert-Butyl (2RS,4SR,5RS)-4-(4-acetamidophenyl) sulphonyl-5-(2-fluorophenyl)-2-pyrrolidinecarboxylate may be prepared as described in Example 1C, but starting with 4.75 g of tert-butyl (2-fluorobenzylideneamino)acetate, 9.5 g of 4-acetamidophenyl vinyl sulphone, 5 g of silver acetate and 3.65 cm³ of triethylamine in 200 cm³ of acetonitrile. After treatment, 4 g of tert-butyl (2RS,4SR,5RS)-4-(4-acetamidophenyl)sulphonyl-5-(2-fluorophenyl)-2-pyrrolidinecarboxylate in the form of a foam, which is used without further purification in the subsequent syntheses, and 1.6 g of tert-butyl (2RS,4RS,5RS)-4-(4-acetamidophenyl) sulphonyl- 5(2-fluorophenyl)-2-pyrrolidinecarboxylate melting at 160° C. are obtained.

D 4-Acetamidophenyl vinyl sulphone may be prepared as described in Example 1E, but starting with 22 g of 4-acetamidophenyl 2-chloroethyl sulphone, 17.8 cm³ of triethylamine and 260 cm³ of tetrahydrofuran. After treatment, 12.7 g of 4-acetamidophenyl vinyl sulphone are obtained, melting at 122° C.

E 4-Acetamidophenyl 2-chloroethyl sulphone may be prepared as described in Example 1F, but starting with 23 g of 4-acetamidophenyl 2-chloroethyl sulphide, 28.6 cm³ of aqueous 30% hydrogen peroxide solution and 150 cm³ of acetic acid. After treatment, 22 g of 4-acetamidophenyl 2-chloroethyl sulphone are obtained, melting at 188° C.

F 4-Acetamidophenyl 2-chloroethyl sulphide may be prepared as described in Example 1G, but starting with 17.6 g of 4-acetamidothiophenol, 0.24 cm³ of aliquat, 4.94 g of sodium hydroxide, 62 cm³ of distilled water and 114 cm³ of 1,2-dichloroethane. After treatment, 23 g of 4-acetamidophenyl 2-chloroethyl sulphide are obtained in the form of a solid melting at 146° C.

EXAMPLE 8

A The process is performed as described in Example 1A, but starting with 1.5 g of tert-butyl (2RS,4SR,5RS)-4-(4-dimethylaminophenyl)sulphonyl-1-{2-[3-(3-ethoxycarbonylphenyl)ureido]acetyl}-5-(2-fluorophenyl)-2-pyrrolidinecarboxylate and 0.12 g of potassium hydroxide in a mixture of 60 cm$^3$ of methanol and 20 cm$^3$ of distilled water. After treatment, 0.12 g of (2RS,4SR,5RS)-3-(3-{2-[2-tert-butoxycarbonyl-4-(4-dimethylaminophenyl)sulphonyl-5-(2-fluorophenyl)-1-pyrrolidinyl]-2-oxoethyl}ureido)benzoic acid is obtained [Rf=0.4; eluent: methylene chloride/methanol (90/10); $^1$H NMR spectrum (250 MHz, (CD$_3$)$_2$SO with addition of a few drops of CD$_3$COOD, at a temperature of 393 K, δ in ppm): 1.52 (s, 9H: C(CH$_3$)$_3$); 2.43 and 2.77 (2 mts, 1H each: CH$_2$ at 3); 3.04 (s, 6H: N(CH$_3$)$_2$); 3.63 and 3.99 (broad d and d respectively, J=17 Hz, 1H each: COCH$_2$N); 3.86 (mt, 1H: H4); 4.56 (broad t, J=8 Hz, 1H: H2); 5.71 (d, J=3 Hz, 1H: H5); 6.81 (d, J=8.5 Hz, 2H: H of the aromatic at 4 (H ortho to the N(CH$_3$)$_2$)); from 7.00 to 7.70 (mt, 6H: aromatic H); 7.68 (d, J=8.5 Hz, 2H: H of the aromatic at 4 (H meta to the N (CH$_3$)$_2$)); 7.80 (mt 1H: H of the aromatic at 5 (H6)); 8.00 (mt, 1H: aromatic H (H2: ortho to the COOH))].

B tert-Butyl (2RS,4SR,5RS)-4-(4-dimethylaminophenyl)sulphonyl-1-{2-[3-(3-ethoxycarbonylphenyl)ureido]acetyl}-5-(2-fluorophenyl)-2-pyrrolidinecarboxylate may be prepared in the following way: to a solution of 1.8 g of tert-butyl (2RS,4SR,5RS)-4-(4-aminophenyl)sulphonyl-1-{2-[3-(3-ethoxycarbonylphenyl)ureido]acetyl}- 5-(2-fluorophenyl)-2-pyrrolidinecarboxylate in 50 cm$^3$ of ethanol are successively added 4 cm$^3$ of formaldehyde and 0.2 g of 10% palladium-on-charcoal. The suspension is stirred for twenty hours at a temperature in the region of 20° C. under a hydrogen atmosphere (130 kPa). The catalyst is separated out by filtration on Celite and the filtrate is concentrated to dryness under reduced pressure. The residue is purified by chromatography on 60 g of silica contained in a column 3.2 cm in diameter [eluent: ethyl acetate/cyclohexane (70/30 by volume)]. The fractions containing the expected product are combined and concentrated under reduced pressure. 1.5 g of tert-butyl (2RS,4SR,5RS)-4-(4-dimethylaminophenyl)sulphonyl-1-{2-[3-(3-ethoxycarbonylphenyl)ureido]acetyl}-5-(2-fluorophenyl)-2-pyrrolidinecarboxylate are obtained in the form of a yellow oil, which is used without further purification in the subsequent syntheses.

C tert-Butyl (2RS,4SR,5RS)-4-(4-aminophenyl)sulphonyl-1-{2-[3-(3-ethoxycarbonylphenyl)ureido]acetyl}-5-(2-fluorophenyl)-2-pyrrolidinecarboxylate may be prepared in the following way: to a solution of 1.9 g of tert-butyl (2RS,4SR,5RS)-1-{2-[3-(3-ethoxycarbonylphenyl)ureido]acetyl}-5-(2-fluorophenyl)-4-(4-nitrophenyl)sulphonyl-2-pyrrolidinecarboxylate in 100 cm$^3$ of ethanol is added 0.2 g of 10% palladium-on-charcoal. The suspension is stirred for twenty hours at a temperature in the region of 20° C. under a hydrogen atmosphere (130 kPa). The catalyst is separated out by filtration on Celite and the filtrate is concentrated to dryness under reduced pressure. 1.8 g of tert-butyl (2RS,4SR,5RS)-4-(4-aminophenyl)sulphonyl-1-{2-[3-(3-ethoxycarbonylphenyl)ureido]acetyl}-5-(2-fluorophenyl)-2-pyrrolidinecarboxylate are thus obtained in the form of a brown oil, which is used without further purification in the subsequent syntheses.

D tert-Butyl (2RS,4SR,5RS)-1-{2-[3-(3-ethoxycarbonylphenyl)ureido]acetyl}-5-(2-fluorophenyl)-4-(4-nitrophenyl)sulphonyl-2-pyrrolidinecarboxylate may be prepared as described in Example 1B, but starting with 1.2 g of tert-butyl (2RS,4SR,5RS)-5-(2-fluorophenyl)-4-(4-nitrophenyl)sulphonyl-2-pyrrolidinecarboxylate, 0.71 g of 2-[3-(3-ethoxycarbonylphenyl)ureido]acetic acid and 0.55 g of N,N'-dicyclohexylcarbodiimide in 50 cm$^3$ of acetonitrile. After treatment, 1.9 g of tert-butyl (2RS,4SR,5RS)-1-{2-[3-(3-ethoxycarbonylphenyl)ureido]acetyl}-5-(2-fluorophenyl)-4-(4-nitrophenyl)sulphonyl-2-pyrrolidinecarboxylate are obtained in the form of a foam, which is used without further purification in the subsequent syntheses.

E 2-[3-(3-Ethoxycarbonylphenyl)ureido]acetic acid may be prepared as described in Example 1H, but starting with 10 g of ethyl 3-isocyanatobenzoate, 3.95 g of glycine and 4.4 g of sodium hydrogen carbonate in 60 cm$^3$ of distilled water. After treatment, 5.3 g of 2-[3-(3-ethoxycarbonylphenyl)ureido]acetic acid are obtained, melting at 174° C.

EXAMPLE 9

A The process is performed as in Example 2A, but starting with 3.4 g of tert-butyl (2RS,4SR,5RS)-1-{2-[3-(3-benzyloxycarbonylphenyl)ureido]acetyl}-5-(2-fluorophenyl)-4-methylsulphonyl-2-pyrrolidinecarboxylate, 0.3 g of 10% palladium-on-charcoal and 100 cm$^3$ of ethanol under a hydrogen atmosphere (130 kPa). After treatment, 2.4 g of (2RS,4SR,5RS)-3-(3-{2-[2-tert-butoxycarbonyl-5-(2-fluorophenyl)-4-methylsulphonyl-1-pyrrolidinyl]-2-oxoethyl}ureido)benzoic acid are obtained [Rf=0.3; eluent: methylene chloride/methanol (90/10); $^1$H NMR spectrum (200 MHz, (CD$_3$)$_2$SO with addition of a few drops of CD$_3$COOD, at a temperature of 373 K, δ in ppm): 1.53 (s, 9H: C(CH$_3$)$_3$); from 2.45 to 2.88 (2 mts, 1H each: CH$_2$ at 3); 3.10 (s, 3H: SO$_2$CH$_3$); 3.70 and 4.02 (broad d and d respectively, J=17 Hz, 1H each: COCH$_2$N); 3.96 (mt, 1H: H4); 4.67 (t, J=8 Hz, 1H: H2); 5.83 (d, J=3 Hz, 1H: H5); from 7.10 to 7.65 (mt, 6H: aromatic H); 7.92 (broad t, J=8 Hz, 1H: H of the aromatic at 5 (H6)); 7.98 (t, J=1.5 Hz, 1H: aromatic H (H2 ortho to the COOH))].

B tert-Butyl (2RS,4SR,5RS)-1-{2-[3-(3-benzyloxycarbonylphenyl)ureido]acetyl}-5-(2-fluorophenyl)-4-methylsulphonyl-2-pyrrolidinecarboxylate may be prepared as described in Example 1B, but starting with 2.2 g of tert-butyl (2RS,4SR,5RS)-5-(2-fluorophenyl)-4-methylsulphonyl-2-pyrrolidinecarboxylate, 2.1 g of 2-[3-(3-benzyloxycarbonylphenyl)ureido]acetic acid and 1.33 g of N,N'-dicyclohexylcarbodiimide in 100 cm$^3$ of acetonitrile. After treatment, 3.4 g of tert-butyl (2RS,4SR,5RS)-1-{2-[3-(3-benzyloxycarbonylphenyl)ureido]acetyl}-5-(2-fluorophenyl)-4-methylsulphonyl-2-pyrrolidinecarboxylate are obtained in the form of a foam, which is used without further purification in the subsequent syntheses.

C tert-Butyl (2RS,4SR,5RS)-5-(2-fluorophenyl)-4-methylsulphonyl-2-pyrrolidinecarboxylate may be prepared as described in Example 1C, but starting with 4.8 g of tert-butyl (2-fluorobenzylideneamino)acetate, 1.8 cm$^3$ of methyl vinyl sulphone, 5 g of silver acetate and 3.5 cm$^3$ of triethylamine in 200 cm$^3$ of acetonitrile. After treatment, 2.2 g of tert-butyl (2RS,4SR,5RS)-5-(2-fluorophenyl)-4-methylsulphonyl-2-pyrrolidinecarboxylate in the form of an orange-coloured oil, which is used without further purification in the subsequent syntheses, and 1.35 g of tert-butyl (2RS,4RS,5RS)-5-(2-fluorophenyl)-4-methylsulphonyl-2-pyrrolidinecarboxylate melting at 176° C. are obtained.

EXAMPLE 10

A The process is performed as in Example 1A, but starting with 3.35 g of (2 RS,4 SR,5RS)-4-(4-chlorophenyl)

sulphonyl-5-(2-fluorophenyl)-2-isobutylcarbamoyl-1-{2-[3-(3-methoxycarbonylmethylphenyl)ureido]acetyl}-pyrrolidine and 0.36 g of potassium hydroxide in a mixture of 60 cm³ of methanol and 20 cm³ of distilled water. After treatment, 1.65 g of 3-(3-{2-[4-(4-chlorophenyl)sulphonyl-5-(2-fluorophenyl)-2-isobutyl carbamoyl-1-pyrrolidinyl]-2-oxoethyl}ureido)phenylacetic acid are obtained [Rf=0.45; eluent: methylene chloride/methanol (90/10); ¹H NMR spectrum (200 MHz, (CD₃)₂SO with addition of a few drops of CD₃COOD, at a temperature of 373 K, δ in ppm): 0.94 (d, J=6.5 Hz, 6H: C(CH₃)₂); 1.85 (mt, 1H: CH); from 2.30 to 2.55 and 2.84 (2 mts, 1H each: CH₂ at 3); 3.06 (mt, 2H: NCH₂); 3.50 (s, 2H: ArCH₂COO); 3.67 and 3.88 (broad d and d respectively, J=17 Hz, 1H each:COCH₂N); 4.08 (mt, 1H: H4); 4.78 (t, J=8 Hz, 1H: H2); 5.68 (d, J=3 Hz, 1H: H5); 6.12 (residual t:NHCO); 6.85 (broad d, J=7.5 Hz, 1H: aromatic H (H4 : ortho to the CH₂)); from 6.95 to 7.30 (mt, 6H: aromatic H); 7.69 (broad d, J=8.5 Hz, 2H: H of the aromatic at 4 (H ortho to the Cl)); 7.96 (broad d, J=8.5 Hz, 2H: H aromatic at 4 (H meta to the Cl)); 8.20 (broad t, J=8 Hz, 1H: H of the aromatic at 5 (H6)); 8.40 (residual s: CONHAr)].

B (2RS,4SR,5RS)-4-(4-Chlorophenyl)sulphonyl-5-(2-fluorophenyl)-2-isobutylcarbamoyl-1-{2-[3-(3-methoxycarbonylmethylphenyl)ureido]acetyl}-pyrrolidine may be prepared as described in Example 1B, but starting with 2.2 g of (2RS,4SR,5RS)-4-(4-chlorophenyl)sulphonyl-5-(2-fluorophenyl)-2-isobutylcarbamoylpyrrolidine, 1.31 g of 2-[3-(3-methoxycarbonylmethylphenyl)ureido]acetic acid and 1.1 g of N,N'-dicyclohexylcarbodiimide in 50 cm³ of acetonitrile. After treatment, 3.35 g of (2RS,4SR,5RS)-4-(4-chlorophenyl)sulphonyl-5-(2-fluorophenyl)-2-isobutylcarbamoyl-1-{2-[3-(3-methoxycarbonylmethylphenyl)ureido]acetyl}-pyrrolidine are obtained in the form of a foam, which is used without further purification in the subsequent syntheses.

C (2RS,4SR,5RS)-4-(4-Chlorophenyl)sulphonyl-5-(2-fluorophenyl)-2-isobutylcarbamoylpyrrolidine may be prepared as described in Example 1C, but starting with 7.6 g of 2-(2-fluorobenzylidene)amino-N-isobutylacetamide, 6.1 g of 4-chlorophenyl vinyl sulphone, 7.52 g of silver acetate and 5.1 cm³ of triethylamine in 200 cm³ of acetonitrile. After treatment, 2.2 g of (2RS,4SR,5RS)-4-(4-chlorophenyl)sulphonyl-5-(2-fluorophenyl)-2-isobutylcarbamoylpyrrolidine in the form of an oil, which is used without further purification in the subsequent syntheses, and 1.3 g of (2RS,4RS,5RS)-4-(4-chlorophenyl)sulphonyl-5-(2-fluorophenyl)-2-isobutylcarbamoylpyrrolidine melting at 136° C. are obtained.

D 2-(2-Fluorobenzylidene)amino-N-isobutylacetamide may be prepared as described in Example 1D, but starting with 3.2 cm³ of 2-fluorobenzaldehyde, 5 g of 2-amino-N-isobutylacetamide hydrochloride, 6 g of 4 Å sieves and 4.2 cm³ of triethylamine in 90 cm³ of dichloromethane. After treatment, 7.6 g of 2-(2-fluorobenzylidene)amino-N-isobutylacetamide are obtained in the form of an oil, which is used without further purification in the subsequent syntheses.

E 2-Amino-N-isobutylacetamide hydrochloride may be prepared in the following way: a solution of 15 g of 2-chloro-N-isobutylacetamide in 145 cm³ of methanolic 7N ammonia solution is stirred for seventy-two hours at a temperature in the region of 20° C. The reaction medium is then concentrated under reduced pressure and the residue crystallized from 50 cm³ of acetonitrile. The solid is isolated by filtration and dried under reduced pressure. 9.3 g of 2-amino-N-isobutylacetamide hydrochloride are thus obtained melting at 154° C.

F 2-Chloro-N-isobutylacetamide may be prepared in the following way: to a solution of 10.2 cm³ of isobutylamine in 50 cm³ of 1,2-dichloroethane are added 25 cm³ of aqueous 20% sodium hydroxide solution. The mixture is cooled to a temperature in the region of −20° C., followed by dropwise addition of 9.9 cm³ of chloroacetyl chloride. The reaction medium is stirred for two hours at a temperature in the region of −20° C., and then for twenty hours at a temperature in the region of 20° C. 100 cm³ of distilled water are then added and the mixture is extracted with three times 100 cm³ of dichloromethane. The organic phases are combined, washed with twice 100 cm³ of aqueous 5% hydrochloric acid solution, twice with 100 cm³ of aqueous 10% sodium hydrogen carbonate solution and twice with 100 cm³ of saturated aqueous sodium chloride solution, then dried over magnesium sulphate and concentrated under reduced pressure. 15 g of 2-chloro-N-isobutylacetamide are thus obtained in the form of a yellow oil, which is used without further purification in the subsequent syntheses.

EXAMPLE 11

A The process is performed as described in Example 2A, but starting with 3.2 g of (2RS,4SR,5RS)-1-{2-[3-(3-benzyloxycarbonylphenyl)ureido]acetyl}-5-(2-fluorophenyl)-4-(2-fluorophenyl)sulphonyl-2-isobutylcarbamoylpyrrolidine, 0.35 g of 10% palladium-on-charcoal and 100 cm³ of ethanol under a hydrogen atmosphere (130 kPa). After treatment, 2.3 g of (2RS,4SR,5RS)-3-(3-{2-[5-(2-fluorophenyl)- 4-(2-fluorophenyl)sulphonyl-2-isobutylcarbamoyl-1-pyrrolidinyl]-2-oxoethyl}ureido)benzoic acid are obtained [Rf=0.3; eluent: methylene chloride/methanol (90/10); ¹H NMR spectrum (200 MHz, (CD₃)₂SO with addition of a few drops of CD₃COOD, at a temperature of 83 K, δ in ppm): 0.96 (d, J=6.5 Hz, 6H: C(CH₃)₂); 1.88 (mt, 1H: CH); from 2.45 to 2.65 and 2.90 (2 mts, 1H each: CH₂ at 3); 3.09 (mt, 2H: NCH₂); 3.70 and 3.90 (broad d and d respectively, J=17 Hz, 1H each: COCH₂N); 4.14 (mt, 1H: H4); 4.86 (t, J=8 Hz, 1H: H2); 5.70 (d, J=3 Hz, 1H: H5); from 6.90 to 8.00 (mt, 10H: aromatic H); 8.00 (mt, 1H: aromatic H (H2: ortho to the COOH)); 8.20 (broad t, J=8 Hz, 1H: H of the aromatic at 5 (H6))].

B (2RS,4SR,5RS)-1-{2-[3-(3-Benzyloxycarbonylphenyl)ureido]acetyl}-5-(2-fluorophenyl)-4-(2-fluorophenyl)sulphonyl-2-isobutylcarbamoylpyrrolidine may be prepared as described in Example 1B, but starting with 2.7 g of (2RS,4SR,5RS)-5-(2-fluorophenyl)-4-(2-fluorophenyl)sulphonyl-2-isobutylcarbamoylpyrrolidine, 2.1 g of 2-[3-(3-benzyloxycarbonylphenyl)ureido]acetic acid and 1.32 g of N,N'-dicyclohexylcarbodiimide in 75 cm³ of acetonitrile. After treatment, 3.2 g of (2RS,4SR,5RS)-1-{2-[3-(3-benzyloxycarbonylphenyl)ureido]acetyl}-5-(2-fluorophenyl)-4-(2-fluorophenyl)sulphonyl-2-isobutylcarbamoylpyrrolidine are obtained in the form of a foam, which is used without further purification in the subsequent syntheses.

C (2RS,4SR,5RS)-5-(2-Fluorophenyl)-4-(2-fluorophenyl)sulphonyl-2-isobutylcarbamoylpyrrolidine may be prepared as described in Example 1C, but starting with 6.3 g of 2-(2-fluorobenzylidene)amino-N-isobutylacetamide, 4.7 g of 2-fluorophenyl vinyl sulphone, 6.32 g of silver acetate and 4.2 cm³ of triethylamine in 200 cm³ of acetonitrile. After treatment, 2.7 g of (2RS,4SR,5RS)-5-(2-fluorophenyl)-4-(2-fluorophenyl)sulphonyl-2- isobutylcarbamoylpyrrolidine in the form of an oil, which is used without further purification in the subsequent syntheses, and 1.55 g of (2RS,4RS,5RS)-5-(2-fluorophenyl)-4-(2-fluorophenyl)sulphonyl-2-isobutylcarbamoylpyrrolidine melting at 128° C. are obtained.

EXAMPLE 12

A The process is performed as described in Example 1A, but starting with 3 g of (2RS,4SR,5RS)-5-(2-fluorophenyl)-2-isobutylcarbamoyl-1-{2-[3-(3-methoxycarbonylphenyl)ureido]acetyl}-4-(3-methoxyphenyl)sulphonylpyrrolidine and 0.245 g of potassium hydroxide in a mixture of 60 cm³ of methanol and 20 cm³ of distilled water. After treatment, 0.5 g of (2RS,4SR,5RS)-3-(3-{2-[5-(2-fluorophenyl)-2-isobutylcarbamoyl-4-(3-methoxyphenyl)sulphonyl-1-pyrrolidinyl]-2-oxoethyl}ureido]benzoic acid is obtained [Rf=0.4; eluent: methylene chloride/methanol (90/10); ¹H NMR spectrum (200 MHz, (CD₃)₂SO with addition of a few drops of CD₃COOD, at a temperature of 383 K, δ in ppm): 0.95 (d, J=6.5 Hz, 6H: C (CH₃)₂); 1.86 (mt, 1H: CH); from 2.35 to 2.55 and 2.86 (2 mts, 1H each: CH₂ at 3); 3.08 (mt, 2H: NCH₂); from 3.60 to 3.80 and 3.90 (mt and d respectively, (J=17 Hz), 1H each: COCH₂N); 3.91 (s, 3H: OCH₃); 4.09 (mt, 1H: H4); 4.81 (t, J=7 Hz, 1H: H2); 5.72 (very broad s, 1H:H5); from 6.95 to 7.65 (mt, 10H: aromatic H); 8.00 (mt, 1H: aromatic H (H2 : ortho to the COOH)); 8.20 (broad t, J=8 Hz, 1H: H of the aromatic at 5 (H6))].

B (2RS,4SR,5RS)-5-(2-Fluorophenyl)-2-isobutylcarbamoyl-1-{2-[3-(3-methoxycarbonylphenyl)ureido]acetyl}-4-(3-methoxyphenyl)sulphonylpyrrolidine may be prepared as described in Example 1B, but starting with 2.2 g of (2RS,4 SR,5RS)-5-(2-fluorophenyl)-2-isobutylcarbamoyl-4-(3-methoxyphenyl)sulphonylpyrrolidine, 1.35 g of 2-[3-(3-methoxycarbonylphenyl)ureido]acetic acid and 1.1 g of N,N'-dicyclohexylcarbodiimide in 100 cm³ of acetonitrile. After treatment, 3 g of (2RS,4 SR,5RS)-5-(2-fluorophenyl)-2-isobutylcarbamoyl-1-{2-[3-(3-methoxycarbonylphenyl)ureido]acetyl}-4-(3-methoxyphenyl)sulphonylpyrrolidine are obtained in the form of a foam, which is used without further purification in the subsequent syntheses.

C (2RS,4SR,5RS)-5-(2-Fluorophenyl)-2-isobutylcarbamoyl-4-(3-methoxyphenyl)sulphonylpyrrolidine may be prepared as described in Example 1C, but starting with 6.3 g of 2-(2-fluorobenzylidene)amino-N-isobutylacetamide, 5 g of 3-methoxyphenyl vinyl sulphone, 6.3 g of silver acetate and 4.6 cm³ of triethylamine in 150 cm³ of acetonitrile. After treatment, 3.8 g of (2RS,4SR,5RS)-5-(2-fluorophenyl)-2-isobutylcarbamoyl-4-(3-methoxyphenyl)sulphonylpyrrolidine in the form of a yellow oil, which is used without further purification in the subsequent syntheses, and 1.7 g of (2RS,4RS,5RS)-5-(2-fluorophenyl)-2-isobutylcarbamoyl-4-(3-methoxyphenyl)sulphonylpyrrolidine hydrochloride melting at 182° C. are obtained.

EXAMPLE 13

A The process is performed as described in Example 1A, but starting with 3 g of (2RS,4SR,5RS)-1-{2-[3-(3-ethoxycarbonylphenyl)ureido]acetyl}-5-(2-fluorophenyl)-2-isobutylcarbamoyl-4-(4-methylphenyl)sulphonylpyrrolidine and 0.252 g of potassium hydroxide in a mixture of 80 cm³ of methanol and 20 cm³ of distilled water. After treatment, 0.18 g of (2RS,4SR,5RS)-3-(3-{2-[5-(2-fluorophenyl)-2-isobutylcarbamoyl-4-(4-methylphenyl)sulphonyl-1-pyrrolidinyl]-2-oxoethyl}ureido)benzoic acid is obtained [Rf=0.6; eluent: methylene chloride/methanol (90/10); ¹H NMR spectrum (200 MHz, (CD₃)₂SO with addition of a few drops of CD₃COOD, at a temperature of 393 K, δ in ppm): 0.96 (d, J=6.5 Hz, 6H: C(CH₃)₂); 1.85 (mt, 1H: CH); from 2.30 to 2.55 and 2.82 (2 mts, 1H each: CH₂ at 3); 2.48 (s, 3H: CH₃); 3.07 (mt, 2H: NCH₂); from 3.60 to 3.80 and 3.88 (mt and d respectively, J=17 Hz), 1H each: COCH₂N); 4.00 (mt, 1H: H4); 4.78 (t, J=7 Hz, 1H: H2); 5.71 (very broad s, 1H: H5); from 6.95 to 7.65 (mt, 6H: aromatic H); 7.49 (d, J=7.5 Hz, 2H: H of the aromatic at 4 (H ortho to the CH₃)); 7.86 (d, J=7.5 Hz, 2H: H of the aromatic at 4 (H meta to the CH₃)); 8.02 (mt, 1H: aromatic H (H2: ortho to the COOH)); 8.22 (broad t, J=8 Hz, 1H: H of the aromatic at 5 (H6))].

B (2RS,4SR,5RS)-1-{2-[3-(3-Ethoxycarbonylphenyl)ureido]acetyl}-5-(2-fluorophenyl)-2-isobutylcarbamoyl-4-(4-methylphenyl)sulphonylpyrrolidine may be prepared as described in Example 1B, but starting with 2.1 g of (2RS,4 SR,5RS)-5-(2-fluorophenyl)-2-isobutylcarbamoyl-4-(4-methylphenyl)sulphonylpyrrolidine, 1.35 g of 2-[3-(3-ethoxycarbonylphenyl)ureido]acetic acid and 1.1 g of N,N'-dicyclohexylcarbodiimide in 100 cm³ of acetonitrile. After treatment, 3 g of (2RS,4SR,5RS)-1-{2-[3-(3-ethoxycarbonylphenyl)ureido]acetyl}-5-(2-fluorophenyl)-2-isobutylcarbamoyl-4-(4-methylphenyl)sulphonylpyrrolidine are obtained in the form of a foam, which is used without further purification in the subsequent syntheses.

C (2RS,4SR,5RS)-5-(2-Fluorophenyl)-2-isobutylcarbamoyl-4-(4-methylphenyl)sulphonylpyrrolidine may be prepared as described in Example 1C, but starting with 10.1 g of 2-(2-fluorobenzylidene)amino-N-isobutylacetamide, 7.3 g of 4-methylphenyl vinyl sulphone, 10.12 g of silver acetate and 7.3 cm³ of triethylamine in 200 cm³ of acetonitrile. After treatment, 5 g of (2RS,4SR,5RS)-5-(2-fluorophenyl)-2-isobutylcarbamoyl-4-(4-methylphenyl)sulphonylpyrrolidine in the form of a yellow oil, which is used without further purification in the subsequent syntheses, and 1.9 g of (2RS,4RS,5RS)-5-(2-fluorophenyl)-2-isobutylcarbamoyl-4-(4-methylphenyl)sulphonylpyrrolidine hydrochloride melting at 234° C. are obtained.

EXAMPLE 14

A The process is performed as described in Example 1A, but starting with 2 g of (2RS,4SR,5RS)-5-(2-fluorophenyl)-2-isobutylcarbamoyl-1-{2-[3-(3-methoxycarbonylphenyl)ureido]acetyl}-4-(4-nitrophenyl)sulphonylpyrrolidine and 0.16 g of potassium hydroxide in a mixture of 60 cm³ of methanol and 20 cm³ of distilled water. After treatment, 0.9 g of (2RS,4SR,5RS)-3-(3-{2-[5-(2-fluorophenyl)-2-isobutylcarbamoyl-4-(4-nitrophenyl)sulphonyl-1-pyrrolidinyl]-2-oxoethyl}ureido)benzoic acid is obtained [Rf=0.2; eluent: methylene chloride/methanol (90/10); ¹H NMR spectrum (200 MHz, (CD₃)₂SO with addition of a few drops of CD₃COOD, at a temperature of 383 K, δ in ppm): 0.94 (d, J=6.5 Hz, 6H: C(CH₃)₂); 1.89 (mt, 1H: CH); from 2.65 to 3.00 (2 mts, 1H each: CH₂ at 3); 3.08 (mt, 2H: NCH₂); 3.72 and 3.91 (broad d and d respectively, J=17 Hz, 1H each: COCH₂N); 4.21 (mt, 1H: H4); 4.83 (t, J=7.5 Hz, 1H: H2); 5.71 (d, J=3 Hz, 1H: H5); from 6.95 to 7.65 (mt, 6H:aromatic H); 8.02 (mt, 1H: aromatic H (H2: ortho to the COOH)); 8.18 (broad t, J=8 Hz, 1H: H of the aromatic at 5 (H6)); 8.25 (d, J=8.5 Hz, 2H: H of the aromatic at 4 (H meta to the NO₂)); 8.42 (d, J=8.5 Hz, 2H: H of the aromatic at 4 (H ortho to the NO₂))].

B (2RS,4SR,5RS)-5-(2-Fluorophenyl)-2-isobutylcarbamoyl-1-{2-[3-(3-methoxycarbonylphenyl)ureido]acetyl}-4-(4-nitrophenyl)sulphonylpyrrolidine may be prepared as described in Example 1B, but starting with 1.35 g of (2RS,4SR,5RS)-5-(2-fluorophenyl)-2-isobutylcarbamoyl-4-(4-nitrophenyl)sulphonylpyrrolidine, 0.76 g of 2-[3-(3-methoxycarbonylphenyl)ureido]acetic acid and 0.62 g of N,N'-dicyclohexylcarbodiimide in 50 cm$^3$ of acetonitrile. After treatment, 2 g of (2RS,4SR,5RS)-5-(2-fluorophenyl)-2-isobutylcarbamoyl-1-{2-[3-(3-methoxycarbonylphenyl)ureido]acetyl}-4-(4-nitrophenyl)sulphonylpyrrolidine are obtained in the form of a foam, which is used without further purification in the subsequent syntheses.

C (2RS,4SR,5RS)-5-(2-Fluorophenyl)-2-isobutylcarbamoyl-4-(4-nitrophenyl)sulphonylpyrrolidine may be prepared as described in Example 1C, but starting with 5.05 g of 2-(2-fluorobenzylidene)amino-N-isobutylacetamide, 4.9 g of 4-nitrophenyl vinyl sulphone, 5.01 g of silver acetate and 3.65 cm$^3$ of triethylamine in 150 cm$^3$ of acetonitrile. After treatment, 2.7 g of (2RS,4SR,5RS)-5-(2-fluorophenyl)-2-isobutylcarbamoyl-4-(4-nitrophenyl)sulphonylpyrrolidine melting at 156° C. and 1.85 g of (2RS,4RS,5RS)-5-(2-fluorophenyl)-2-isobutylcarbamoyl-4-(4-nitrophenyl)sulphonylpyrrolidine melting at 218° C. are obtained.

EXAMPLE 15

A The process is performed as described in Example 6A, but starting with 2 g of (2RS,4SR,5RS)-1-{2-[3-(3-benzyloxycarbonylphenyl)ureido]acetyl}-5-(2-fluorophenyl)-2-isobutylcarbamoyl-4-(4-nitrophenyl)sulphonylpyrrolidine, 0.2 g of 10% palladium-on-charcoal and 100 cm$^3$ of ethanol under a hydrogen atmosphere (130 kPa). After treatment, 1.15 g of (2RS,4SR,5RS)-3-(3-{2-[4-(4-aminophenyl)sulphonyl-5-(2-fluorophenyl)-2-isobutylcarbamoyl-1-pyrrolidinyl]-2-oxoethyl}ureido)phenylacetic acid are obtained [Rf=0.3; eluent: methylene chloride/methanol (90/10); $^1$H NMR spectrum (200 MHz, (CD$_3$)$_2$SO, at a temperature of 383 K, δ in ppm): 0.97 (d, J=6.5 Hz, 6H: C(CH$_3$)$_2$); 1.87 (mt, 1H: CH); 2.40 and 2.79 (2 mts, 1H each: CH$_2$ at 3); 3.09 (mt, 2H: NCH$_2$); 3.70 and 3.92 (broad d and dd respectively, J=17 Hz and J=17 and 5.5 Hz: 1H each: COCH$_2$N); 3.82 (mt, 1H: H4); 4.78 (t, J=7.5 Hz, 1H: H2); 5.71 (d, J=3 Hz, 1H: H5); from 5.60 to 5.90 (broad mult., 2H: NH$_2$); 6.15 (t, J=5.5 Hz, 1H: NHCO); 6.77 (d, J=8.5 Hz, 2H: H of the aromatic at 4 (H ortho to the NH$_2$)); from 7.00 to 7.70 (mt, 6H: aromatic H); 7.58 (d, J=8.5 Hz, 2H: H of the aromatic at 4 (H meta to the NH$_2$)); 7.90 (mult., 1H: NH); 8.02 (mt, 1H: aromatic H (H2: ortho to the COOH)); 8.20 (broad t, J=8 Hz, 1H: H of the aromatic at 5 (H6)); 8.60 (s, 1H: CONHAr)].

B (2RS,4SR,5RS)-1-{2-[3-(3-Benzyloxycarbonylphenyl)ureido]acetyl}-5-(2-fluorophenyl)-2-isobutylcarbamoyl-4-(4-nitrophenyl)sulphonylpyrrolidine may be prepared as described in Example 1B, but starting with 1.31 g of (2RS,4SR,5RS)-5-(2-fluorophenyl)-2-isobutylcarbamoyl-4-(4-nitrophenyl)sulphonylpyrrolidine, 0.97 g of 2-[3-(3-benzyloxycarbonylphenyl)ureido]acetic acid and 0.62 g of N,N'-dicyclohexylcarbodiimide in 50 cm$^3$ of acetonitrile. After treatment, 2 g of (2RS,4SR,5RS)-1-{2-[3-(3-benzyloxycarbonylphenyl)ureido]acetyl}-5-(2-fluorophenyl)-2-isobutylcarbamoyl-4-(4-nitrophenyl)sulphonylpyrrolidine are obtained in the form of a foam, which is used without further purification in the subsequent syntheses.

EXAMPLE 16

A The process is performed as described in Example 2A, but starting with 1.6 g of (2RS,4SR,5RS)-4-(4-acetamidophenyl)sulphonyl- 1-{2-[3-(3-benzyloxycarbonylphenyl)ureido]acetyl}-5-(2-fluorophenyl)-2-isobutylcarbamoylpyrrolidine, 0.2 g of 10% palladium-on-charcoal and 100 cm$^3$ of ethanol under a hydrogen atmosphere (130 kPa). After treatment, 1.05 g of (2RS,4SR,5RS)-3-(3-{2-[4-(4-acetamidophenyl)sulphonyl-5-(2-fluorophenyl)-2-isobutylcarbamoyl-1-pyrrolidinyl]-2-oxoethyl}ureido)benzoic acid are obtained [Rf=0.2 eluent: methylene chloride/methanol (90/10); $^1$H NMR spectrum (300 MHz, (CD$_3$)$_2$SO, at a temperature of 383 K, δ in ppm): 0.97 (d, J=6.5 Hz, 6H: C(CH$_3$)$_2$); 1.85 (mt, 1H: CH); 2.15 (s, 3H: COH$_3$); 2.41 and 2.82 (2 mts, 1H each: CH$_2$ at 3); 3.08 (mt, 2H: NCH$_2$); 3.70 and 3.89 (mt and dd respectively, (J=17 and 5.5 Hz), 1H each: COCH$_2$N); 3.98 (mt, 1H: H4); 4.79 (t, J=7.5 Hz, 1H: H2); 5.71 (mt, 1H: H5); 6.18 (t, J=5.5 Hz, 1H: NHCO); from 7.00 to 7.65 (mt, 6H: aromatic H); 7.86 (limiting AB, 4H: H of the aromatic at H4); 8.00 (mt, 1H: aromatic H (H2: ortho to the COOH)); 8.03 (mult., 1H: NH); 8.23 (broad t, J=8 Hz, 1H: H of the aromatic at 5 (H6)); 8.67 (s, 1H: CONHAr); 10.03 (s, 1H: ArNH)].

B (2RS,4 SR,5RS)-4-(4-Acetamidophenyl)sulphonyl-1-{2-[3-(3-benzyloxycarbonylphenyl)ureido]acetyl}-5-(2-fluorophenyl)-2-isobutylcarbamoylpyrrolidine may be prepared as described in Example 1B, but starting with 1.16 g of (2RS,4SR,5RS)-4-(4-acetamidophenyl)sulphonyl-5-(2-fluorophenyl)- 2-isobutylcarbamoylpyrrolidine, 0.82 g of 2-[3-(3-benzyloxycarbonylphenyl)ureido]acetic acid and 0.52 g of N,N'-dicyclohexylcarbodiimide in 100 cm$^3$ of acetonitrile. After treatment, 1.6 g of (2RS,4SR,5RS)-4-(4-acetamidophenyl)sulphonyl-1-{2-[3-(3-benzyloxycarbonylphenyl)ureido]acetyl}-5-(2-fluorophenyl)-2-isobutylcarbamoylpyrrolidine are obtained in the form of a foam, which is used without further purification in the subsequent syntheses.

C (2RS,4SR,5RS)-4-(4-Acetamidophenyl)sulphonyl-5-(2-fluorophenyl)-2-isobutylcarbamoylpyrrolidine may be prepared as described in Example 1C, but starting with 2.55 g of 2-(2-fluorobenzylidene)amino-N-isobutylacetamide, 2.25 g of 4-acetamidophenyl vinyl sulphone, 2.5 g of silver acetate and 1.85 cm$^3$ of triethylamine in 100 cm$^3$ of acetonitrile. After treatment, 1.2 g of (2RS,4SR,5RS)-4-(4-acetamidophenyl)sulphonyl-5-(2-fluorophenyl)-2-isobutylcarbamoylpyrrolidine in the form of a foam, which is used without further purification in the subsequent syntheses, and 0.9 g of (2RS,4RS,5RS)-4-(4-acetamidophenyl)sulphonyl-5-(2-fluorophenyl)-2-isobutylcarbamoylpyrrolidine are obtained.

EXAMPLE 17

A The process is performed as described in Example 2A, but starting with 2.5 g of (2RS,4SR,5RS)-1-{2-[3-(3-benzyloxycarbonylphenyl)ureido]acetyl}-2-tert-butoxycarbonyl-5-(2-fluorophenyl)-4-morpholinosulphonylpyrrolidine, 0.25 g of 10% palladium-on-charcoal and 100 cm$^3$ of ethanol under a hydrogen atmosphere (130 kPa). After treatment, 1.3 g of (2RS,4SR,5RS)-3-(3-{2-[2-tert-butoxycarbonyl-5-(2-fluorophenyl)-4-morpholinosulphonyl-1-pyrrolidinyl]-2-oxoethyl}ureido) benzoic acid are obtained [Rf=0.43; eluent: methylene chloride/methanol (90/10)].

B (2RS,4SR,5RS)-1-{2-[3-(3-Benzyloxycarbonylphenyl)ureido]acetyl}-2-tert-butoxycarbonyl-5-(2-fluorophenyl)-4-morpholinosulphonylpyrrolidine may be prepared as described in Example 1B, but starting with 2 g of (2RS,4SR,5RS)-2-tert-butoxycarbonyl-5-(2-fluorophenyl)-4-morpholinosulphonylpyrrolidine, 1.58 g of 2-[3-(3- benzyloxycarbonylphenyl)ureido]acetic acid and 0.99 g of N,N'-dicyclohexylcarbodiimide in 50 cm³ of acetonitrile. After treatment, 2.5 g of (2RS,4SR,5RS)-1-{2-[3-(3-benzyloxycarbonylphenyl)ureido]acetyl}-2-tert-butoxycarbonyl-5-(2-fluorophenyl)-4-morpholinosulphonylpyrrolidine are obtained in the form of an amorphous solid, which is used without further purification in the subsequent syntheses.

C (2RS,4SR,5RS)-2-tert-Butoxycarbonyl-5-(2-fluorophenyl)-4-morpholinosulphonylpyrrolidine may be prepared as described in Example 1C, but starting with 4.8 g of tert-butyl (2-fluorobenzylideneamino)acetate, 3.75 g of 1-vinylsulphonylmorpholine, 5 g of silver acetate and 3.6 cm³ of triethylamine in 200 cm³ of acetonitrile. After treatment, 2 g of (2RS,4SR,5RS)-2-tert-butoxycarbonyl-5-(2-fluorophenyl)-4-morpholinosulphonylpyrrolidine in the form of an oil, which is used without further purification in the subsequent syntheses, and 1 g of (2RS,4RS,5RS)-2-tert-butoxycarbonyl-5-(2-fluorophenyl)-4-morpholinosulphonylpyrrolidine melting at 130° C. are obtained.

1-Vinylsulphonylmorpholine may be prepared according to the method described by J. Chanet-Rey et al., Heterocycles, 26, 101 (1987).

EXAMPLE 18

A The process is performed as described in Example 2A, but starting with 3 g of (2RS,4SR,5RS)-1-{2-[3-(3-benzyloxycarbonylphenyl)ureido]acetyl}-5-(2-fluorophenyl)-4-morpholinosulphonyl-2-(3,3-dimethylbutyl)carbamoylpyrrolidine, 0.3 g of 10% palladium-on-charcoal and 100 cm³ of ethanol under a hydrogen atmosphere (130 kPa). After treatment, 2.2 g of (2RS,4SR,5RS)-3-(3-{2-[2-(3,3-dimethylbutyl)carbamoyl-5-(2-fluorophenyl)-4-morpholinosulphonyl-1-pyrrolidinyl]-2-oxoethyl}ureido)benzoic acid are obtained [Rf=0.25; eluent: methylene chloride/methanol (90/10)].

B (2RS,4SR,5RS)-1-{2-[3-(3-Benzyloxycarbonylphenyl)ureido]acetyl}-5-(2-fluorophenyl)-4-morpholinosulphonyl-2-(3,3-dimethylbutyl)carbamoylpyrrolidine may be prepared as described in Example 1B, but starting with 2.4 g of (2RS,4SR,5RS)-5-(2-fluorophenyl)-4-morpholinosulphonyl-2-(3,3-dimethylbutyl)carbamoylpyrrolidine, 1.78 g of 2-[3-(3-benzyloxycarbonylphenyl)ureido]acetic acid and 1.15 g of N,N'-dicyclohexylcarbodiimide in 100 cm³ of acetonitrile. After treatment, 3 g of (2RS,4SR,5RS)-1-{2-[3-(3-benzyloxycarbonylphenyl)ureido]acetyl}-5-(2-fluorophenyl)-4-morpholinosulphonyl-2-(3,3-dimethylbutyl)carbamoylpyrrolidine are obtained in the form of a foam, which is used without further purification in the subsequent syntheses.

C (2RS,4SR,5RS)-5-(2-Fluorophenyl)-4-morpholinosulphonyl-2-(3,3-dimethylbutyl)carbamoylpyrrolidine may be prepared in the following way: to a solution of 3 g of (2RS,4SR,5RS)-1-tert-butoxycarbonyl-5-(2-fluorophenyl)-4-morpholinosulphonyl-2-(3,3-dimethylbutyl)carbamoylpyrrolidine in 100 cm³ of chloroform is added 0.79 cm³ of iodotrimethylsilane. The reaction mixture is stirred for twenty hours at a temperature in the region of 20° C., and then poured into 100 cm³ of saturated sodium bicarbonate solution. The organic phase is separated out after settling of the phases has taken place, washed with 75 cm³ of water, dried over magnesium sulphate and concentrated under reduced pressure. 2.4 g of (2RS,4SR,5RS)-5-(2-fluorophenyl)-4-morpholinosulphonyl-2-(3,3-dimethylbutyl)carbamoylpyrrolidine are thus obtained in the form of an oil, which is used without further purification in the subsequent syntheses.

D (2RS,4SR,5RS)-1-tert-Butoxycarbonyl-5-(2-fluorophenyl)-4-morpholinosulphonyl-2-(3,3-dimethylbutyl)carbamoylpyrrolidine may be prepared in the following way: to a solution of 2.6 g of (2RS,4SR,5RS)-1-tert-butoxycarbonyl-5-(2-fluorophenyl)-4-morpholinosulphonyl-2-pyrrolidinecarboxylic acid in 50 cm³ of 1,2-dichloroethane are successively added 1.01 g of N,N'-carbonyldiimidazole and 0.05 g of 4-dimethylaminopyridine. The reaction mixture is stirred for 2 hours at a temperature in the region of 20° C., followed by dropwise addition of a solution of 0.77 cm³ of 3,3-dimethylbutylamine in 25 cm³ of 1,2-dichloroethane. The reaction mixture is stirred for a further 20 hours at a temperature in the region of 20° C., and then washed successively with 75 cm³ of water, with twice 75 cm³ of aqueous decinormal hydrochloric acid solution, with 25 cm³ of water, with twice 75 cm³ of aqueous decinormal sodium hydroxide solution and with 75 cm³ of saturated aqueous sodium chloride solution. The organic phase is dried over magnesium sulphate and concentrated under reduced pressure. The residue is taken up in 50 cm³ of pentane and filtered. 3 g of (2RS,4SR,5RS)-1-tert-butoxycarbonyl-5-(2-fluorophenyl)-4-morpholinosulphonyl-2-(3,3-dimethylbutyl)carbamoylpyrrolidine are thus obtained in the form of a foam, which is used without further purification in the subsequent syntheses.

E (2RS,4SR,5RS)-1-tert-Butoxycarbonyl-5-(2-fluorophenyl)-4-morpholinosulphonyl-2-pyrrolidinecarboxylic acid may be prepared in the following way: to a solution of 2.6 g of (2RS,4SR,5RS)-5-(2-fluorophenyl)-4-morpholinosulphonyl-2-pyrrolidinecarboxylic acid hydrochloride and 1.4 g of sodium carbonate in 60 cm³ of distilled water is added dropwise a solution of 1.6 g of di-tert-butyl dicarbonate in 30 cm³ of 1,4-dioxane. The reaction medium is stirred for 20 hours at a temperature in the region of 20° C., followed by addition of 50 cm³ of distilled water. The aqueous phase is washed with twice 50 cm³ of ethyl acetate and then brought to a pH in the region of 1 by addition of aqueous tetranormal hydrochloric acid solution, and extracted with three times 75 cm³ of ethyl acetate. The organic extracts are combined and washed with 50 cm³ of saturated aqueous sodium chloride solution, dried over magnesium sulphate and concentrated under reduced pressure. 2.6 g of (2RS,4SR,5RS)-1-tert-butoxycarbonyl-5-(2-fluorophenyl)-4-morpholinosulphonyl-2-pyrrolidinecarboxylic acid are thus obtained in the form of a foam, which is used without further purification in the subsequent syntheses.

F (2RS,4SR,5RS)-5-(2-Fluorophenyl)-4-morpholinosulphonyl-2-pyrrolidinecarboxylic acid hydrochloride may be prepared in the following way: to a solution of 2.7 g of (2RS,4SR,5RS)-5-(2-fluorophenyl)-2-methoxycarbonyl-4-morpholinosulphonylpyrrolidine in a mixture of 60 cm³ of methanol and 30 cm³ of distilled water is added 0.4 g of potassium hydroxide. The reaction medium is stirred for 8 hours at a temperature in the region of 20° C., and then concentrated under reduced pressure. The residue is dissolved in 150 cm³ of distilled water and the aqueous phase is washed with twice 50 cm³ of diethyl ether, brought to a pH in the region of 1 by addition of aqueous tetranormal hydrochloric acid solution and concentrated under reduced pressure. The residue is taken up in 75 cm³ of a dichloromethane/methanol mixture (80/20 by volume). The insoluble product is isolated by filtration and extracted with twice 50 cm³ of a dichloromethane/methanol mixture (80/20 by volume). The filtrate is concentrated under reduced pressure. 2.6 g of (2RS,4SR,5RS)-5-(2-fluorophenyl)-4-morpholinosulphonyl-2-pyrrolidinecarboxylic acid hydrochloride are thus obtained in the form of an oil, which is used without further purification in the subsequent syntheses.

G (2RS,4SR,5RS)-5-(2-Fluorophenyl)-2-methoxycarbonyl-4-morpholinosulphonylpyrrolidine may be prepared as described in Example 1C, but starting with 7.9 g of methyl (2-fluorobenzylideneamino)acetate, 7.5 g of 1-vinylsulphonylmorpholine, 10 g of silver acetate and 6.8 cm³ of triethylamine in 300 cm³ of acetonitrile. After treatment, 2.7 g of (2RS,4SR,5RS)-5-(2-fluorophenyl)-2-methoxycarbonyl-4-morpholinosulphonylpyrrolidine in the form of an oil, which is used without further purification in the subsequent syntheses, and 1.7 g of (2RS,4RS,5RS)-5-(2-fluorophenyl)-2-methoxycarbonyl-4-morpholinosulphonylpyrrolidine melting at 156° C. are obtained.

H Methyl (2-fluorobenzylideneamino)acetate may be prepared as described in Example 1D, but starting with 4.25 cm³ of 2-fluorobenzaldehyde, 5.12 g of methyl glycinate hydrochloride, 12 g of 4 Å sieves and 5.6 cm³ of triethylamine in 100 cm³ of dichloromethane. After treatment, 7.9 g of methyl (2-fluorobenzylideneamino)acetate are obtained in the form of an oil, which is used without further purification in the subsequent syntheses.

The medicaments according to the invention consist of a compound of formula (I) in free form or in the form of a pharmaceutically acceptable salt, in pure form or in the form of a composition in which it is combined with any other pharmaceutically compatible product, which may be inert or physiologically active. The medicaments according to the invention may be employed via the oral, parenteral, rectal or topical route.

As solid compositions for oral administration, tablets, pills, powders (gelatine capsules and cachets) or granules may be used. In these compositions, the active principle according to the invention is mixed with one or more inert diluents, such as starch, cellulose, succrose, lactose or silica. These compositions may also comprise substances other than diluents, for example one or more lubricants such as magnesium stearate or talc, a dye, a coating (dragees) or a varnish.

As liquid compositions for oral administration, pharmaceutically acceptable solutions, suspensions, emulsions, syrups and elixirs containing inert diluents such as water, ethanol, glycerol, vegetable oils or paraffin oil, may be used. These compositions may comprise substances other than diluents, for example wetting, sweetening, thickening, flavouring or stabilizing agents.

The sterile compositions for parenteral administration may preferably be solutions, aqueous or non-aqueous, suspensions or emulsions. As solvent or vehicle, water, propylene glycol, a polyethylene glycol, vegetable oils, in particular olive oil, injectable organic esters, for example ethyl oleate, or other suitable organic solvents may be employed. These compositions may also contain adjuvants, in particular wetting, tonicity, emulsifying, dispersing and stabilizing agents. The sterilization may be performed in several ways, for example by aseptic filtration, by incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which contain, besides the active product, excipients such as cocoa butter, semi-synthetic glycerides or polyethylene glycols.

The compositions for topical administration may, for example, be creams, lotions, eye drops, mouth washes, nasal drops or aerosols.

In human therapy, the compounds according to the invention are particularly useful in the treatment and prevention of disorders linked to CCK and to gastrin in the nervous system and in the gastrointestinal system. These compounds may thus be used in the treatment and prevention of psychosis, anxiety disorders, depression, neurodegeneration, panic attacks, Parkinson's disease, tardive dyskinesia, irritable bowel syndrome, acute pancreatitis, ulcers, intestinal motility disorders, certain CCK-sensitive tumours and memory disorders, in withdrawal from chronic treatments and alcohol or drug abuse, as constrictors of the pupil of the eye, as analgesics, as potentiators of the analgesic activity of narcotic and non-narcotic analgesic drugs and as appetite regulators.

The doses depend upon the desired effect, the duration of the treatment and the route of administration used; they are generally between 0.05 g and 1 g per day via the oral route for an adult, with unit doses ranging from 10 mg to 500 mg of active substance.

Generally speaking, the doctor will determine the appropriate dosage depending on the age, the weight and all the other factors specific to the person to be treated.

The examples which follow illustrate compositions according to the invention:

EXAMPLE A

Gelatin capsules containing a 50 mg dose of active product and having the following composition are prepared according to the usual technique:

Compound of formula (I) 50 mg

Cellulose 18 mg

Lactose 55 mg

Colloidal silica 1 mg

Sodium carboxymethylstarch 10 mg

Talc 10 mg

Magnesium stearate 1 mg

EXAMPLE B

Tablets containing a 50 mg dose of active product and having the following composition are prepared according to the usual technique:

Compound of formula (I) 50 mg

Lactose 104 mg

Cellulose 40 mg

Polyvidone 10 mg

Sodium carboxymethylstarch 22 mg

Talc 10 mg

Magnesium stearate 2 mg

Colloidal silica 2 mg

Mixture of hydroxymethylcellulose, glycerol and titanium oxide (72-3.5-24.5) qs 1 finished film-coated tablet containing 245 mg

EXAMPLE C

An injectable solution containing 10 mg of active product and having the following composition is prepared:

Compound of formula (I) 10 mg
Benzoic acid 80 mg
Benzyl alcohol 0.06 cm³
Sodium benzoate 80 mg
95% Ethanol 0.4 cm³
Sodium hydroxide 24 mg
Propylene glycol 1.6 cm³
Water qs 4 cm³

We claim:

1. A compound of formula (I):

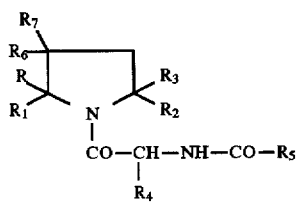

(I)

in which
R represents an alkyl radical containing 1 to 12 carbon atoms in a straight or branched chain, wherein said radical may be mono- or polyunsaturated; a cycloalkyl radical containing 3 to 12 carbon atoms, wherein said radical may be mono- or polyunsaturated; a polycycloalkyl radical containing 6 to 12 carbon atoms, wherein said radical may be mono- or polyunsaturated; a phenylalkyl radical in which the phenyl ring may be substituted with one or more substituents selected from alkyl radicals, alkoxy radicals, and halogen atoms; a diphenylalkyl radical; a cinnamyl radical; a pyridyl radical which may be substituted with one or more alkyl radicals; a furyl radical which may be substituted with one or more alkyl radicals; a thienyl radical which may be substituted with one or more alkyl radicals; a quinolyl radical which may be substituted with one or more alkyl radicals; a naphthyl radical which may be substituted with one or more alkyl radicals; an indolyl radical which may be substituted with one or more alkyl radicals; or a phenyl radical which may be substituted with one or more substituents selected from halogen atoms and alkyl, alkoxy, hydroxyl, nitro, amino, monoalkylamino, dialkylamino, alkoxycarbonyl, —CO—NR$_8$R$_9$, —NH—CO—CH$_3$, trifluoromethyl and trifluoromethoxy radicals;

R$_1$ represents a hydrogen atom or an alkyl radical;

R$_2$ represents a —(CH$_2$)$_n$—CO—R$_{10}$, —(CH$_2$)$_m$—O—CO—R$_{11}$ or —(CH$_2$)$_m$—NR$_{12}$R$_{13}$ chain, an oxazolinyl radical which may be substituted with one or more alkyl radicals, or a 3-alkyloxadiazolyl radical;

R$_3$ represents a hydrogen atom or an alkyl radical;

R$_4$ represents a hydrogen atom or an alkyl radical;

R$_5$ represents a phenyl radical which may be substituted with one or more substituents selected from halogen atoms and alkyl, alkoxy and alkylthio radicals; a naphthyl radical; an indolyl radical; an quinolyl radical; or a phenylamino radical in which the phenyl ring may be substituted with one or more substituents selected from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho,-alk-O—CO-alk,-alk-COOX,-alk-O-alk,-alk'-COOX, —O-alk-COOX, —CH=CH—COOX, —CO—COOX, -alk-SO$_3$H in salt form, —CH=CH-alk', —C(=NOH)—COOX, —S-alk-COOX, —SO-alk-COOX, —SO$_2$-alk-COOX, —O—CH$_2$-alk'-COOX, —CX=N—O-alk-COOX, -alk-N(OH)—CO-alk, -alk-SO$_2$H, —SO$_2$—NH—CO—R$_{14}$, —SO$_2$—NH—SO$_2$—R$_{14}$, —CO—NH—CO—R$_{14}$, —CO—NH—SO$_2$—R$_{14}$, —B(OH)$_2$, —C(NH$_2$)=NOH, —SO$_2$—NH—R$_{15}$, —CO—NH—R$_{15}$,

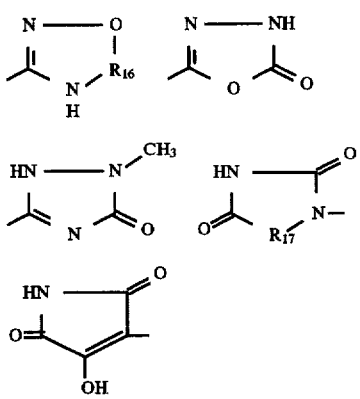

and 2,2-dimethyl-4,6-dioxo-1,3-dioxan-5-yl radicals;

R$_6$ represents a hydrogen atom or an alkyl or phenylalkyl radical;

R$_7$ represents an alkylsulphonyl radical, a —SO$_2$—NR$_8$R$_9$ radical or a phenylsulphonyl radical in which the phenyl ring is substituted with one or more substituents selected from halogen atoms and alkyl, alkoxy, hydroxyl, nitro, amino, monoalkylamino, dialkylamino, acylamino, trifluoromethyl and trifluoromethoxy radicals;

R$_8$ represents a hydrogen atom, an alkyl radical, a phenylalkyl radical, or a phenyl radical which may be substituted with one or more substituents selected from halogen atoms and alkyl, alkoxy and alkylthio radicals;

R$_9$ represents an alkyl radical, a phenylalkyl radical or a phenyl radical which may be substituted with one or more substituents selected from halogen atoms and alkyl, alkoxy and alkylthio radicals;

or R$_8$ and R$_9$ form, together with the nitrogen atom to which they are attached, a saturated or unsaturated mono- or polycyclic heterocycle containing 4 to 9 carbon atoms and one or more hetero atoms selected from oxygen and nitrogen, and which may be substituted with one or more alkyl radicals;

R$_{10}$ represents a hydroxyl, alkoxy, cycloalkyloxy, cycloalkylalkyloxy, phenyl or —NR$_{12}$R$_{13}$ radical;

R$_{11}$ represents an alkoxy, cycloalkyloxy, cycloalkylalkyloxy, phenyl or —NR$_{12}$R$_{13}$ radical;

R$_{12}$ represents a hydrogen atom, an alkyl, cycloalkylalkyl, cycloalkyl or phenylalkyl radical or a phenyl radical which may be substituted with one or more substituents selected from halogen atoms and alkyl, alkoxy and alkylthio radicals;

R$_{13}$ represents an alkyl, cycloalkylalkyl, cycloalkyl or phenylalkyl radical or a phenyl radical which may be substituted with one or more substituents selected from halogen atoms and alkyl, alkoxy and alkylthio radicals;

or R$_{12}$ and R$_{13}$ form, together with the nitrogen atom to which they are attached, a saturated or unsaturated mono- or polycyclic heterocycle containing 4 to 9 carbon atoms and one or more hetero atoms selected from oxygen, nitrogen and sulfur, and which may be substituted with one or more alkyl radicals;

$R_{14}$ represents an alkyl, cycloalkyl or trifluoromethyl radical or a phenyl radical which may be substituted with one or more substituents selected from cyano, alkoxy, nitro and amino radicals and halogen atoms;

$R_{15}$ represents a 5-tetrazolyl radical;

$R_{16}$ represents C=O or S=O;

$R_{17}$ represents O or C=O;

n is equal to 0, 1 or 2;

m is equal to 1 or 2;

X represents a hydrogen atom or an alkyl or phenylalkyl radical;

alk represents an alkyl or alkylene radical;

alk' represents a hydroxyalkyl, hydroxyalkylene, alkoxyalkyl or alkoxyalkylene radical;

it being understood that, except where otherwise mentioned, said alkyl, alkylene and alkoxy radicals and said alkyl, alkylene and alkoxy portions of radicals contain 1 to 4 carbon atoms in a straight or branched chain, said acyl radicals and said acyl portions of radicals contain 2 to 4 carbon atoms, and said cycloalkyl radicals and said cycloalkyl portions of radicals contain 3 to 6 carbon atoms;

a racemic mixture of a compound of formula (I), an enantiomer of a compound of formula (I), or a salt of a compound of formula (I).

2. A compound of formula (I) according to claim 1, for which R represents an isopropylidene, cyclohexyl, tetrahydrophenyl, cyclopentadienyl, dihydrophenyl, norbornyl, adamantyl or norbornenyl radical;

or a racemic mixture, an enantiomer or a salt thereof.

3. A compound of formula (I) according to claim 1, for which, when $R_8$ and $R_9$ form, together with the nitrogen atom to which they are attached, a heterocycle, wherein said heterocycle is a piperidino ring which may be substituted with one or more alkyl radicals, a morpholino ring or a 1,2,3,4-tetrahydroquinoline ring system;

or a racemic mixture, an enantiomer, or a salt thereof.

4. A compound of formula (I) according to claim 1, for which, when and $R_{13}$ form, together with the nitrogen atom to which they are attached, a heterocycle, wherein said heterocycle is a piperidino, perhydro-1-azepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino or 1-indolinyl ring system, and further wherein each of said ring systems may be substituted with at least one alkyl radical;

or a racemic mixture, an enantiomer, or a salt thereof.

5. A compound of formula (I) according to claim 1, for which:

R represents a phenyl radical which may be substituted with one or more substituents selected from halogen atoms and alkyl, alkoxy, hydroxyl, nitro, amino, monoalkylamino, dialkylamino, alkoxycarbonyl, —CO—NR$_8$R$_9$, —NH—CO—CH$_3$, trifluoromethyl and trifluoromethoxy radicals;

$R_1$ represents a hydrogen atom;

$R_2$ represents a —(CH$_2$)$_n$—CO—R$_{10}$ chain;

$R_3$ represents a hydrogen atom;

$R_4$ represents a hydrogen atom;

$R_5$ represents a phenylamino radical in which the phenyl ring may be substituted with one or more substituents selected from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono-or polyhydroxyalkyl, sulpho, -alk-O—CO-alk, -alk-COOX, -alk-O-alk, -alk'-COOX, —O-alk-COOX, —CH=CH—COOX, —CO—COOX, -alk-SO$_3$H in salt form, —CH=CH-alk', —C(=NOH)—COOX, —S-alk-COOX, —SO-alk-COOX, —SO$_2$-alk-COOX, —O—CH$_2$-alk'—COOX, —CX=N—O-alk-COOX, -alk-N(OH)—CO-alk, -alk-SO$_2$H, —SO$_2$—NH—CO—R$_{14}$, —SO$_2$—NH—SO$_2$-R$_{14}$, —CO—NH—CO—R$_{14}$, —CO—NH—SO$_2$—R$_{14}$, —B(OH)$_2$, —C(NH$_2$)=NOH, —SO$_2$—NH—R$_{15}$, —CO—NH—R$_{15}$.

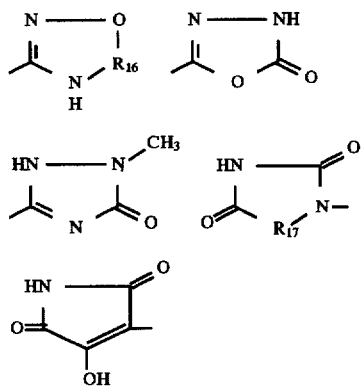

and 2,2-dimethyl-4,6-dioxo-1,3-dioxan-5-yl radicals;

$R_6$ represents a hydrogen atom;

$R_7$ represents an alkylsulphonyl radical; a —SO$_2$—NR$_8$R$_9$ radical or a phenylsulphonyl radical in which the phenyl ring is substituted with one or more substituents selected from halogen atoms and alkyl, alkoxy, hydroxyl, nitro, amino, monoalkylamino, dialkylamino, acylamino, trifluoromethyl and trifluoromethoxy radicals;

$R_8$ represents a hydrogen atom, an alkyl or phenylalkyl radical or a phenyl radical which may be substituted with one or more substituents selected from halogen atoms and alkyl, alkoxy and alkylthio radicals;

$R_9$ represents an alkyl or phenylalkyl radical or a phenyl radical which may be substituted with one or more substituents selected from halogen atoms and alkyl, alkoxy and alkylthio radicals;

or $R_8$ and $R_9$ form, together with the nitrogen atom to which they are attached, a saturated or unsaturated mono- or polycyclic heterocycle containing 4 to 9 carbon atoms and one or more hetero atoms selected from oxygen and nitrogen, and which may be substituted with one or more alkyl radicals;

$R_{10}$ represents a hydroxyl or alkoxy radical;

$R_{14}$ represents an alkyl, cycloalkyl or trifluoromethyl radical or a phenyl radical which may be substituted with one or more substituents selected from cyano, alkoxy, nitro and amino radicals and halogen atoms;

$R_{15}$ represents a 5-tetrazolyl radical;

$R_{16}$ represents C=O or S=O;

$R_{17}$ represents O or C=O;

n is equal to 0, 1 or 2;

X represents a hydrogen atom or an alkyl or phenylalkyl radical alk represents an alkyl or alkylene radical;

alk' represents a hydroxyalkyl, hydroxyalkylene, alkoxyalkyl or alkoxyalkylene radical;

or a racemic mixture, an enantiomer, or a salt thereof.

6. A compound selected from (2RS,4SR,5RS)-3-(3-{2-[2-tert-butoxycarbonyl-5-(2-fluorophenyl)-4-(4-chlorophenyl)sulphonyl-1-pyrrolidinyl]-2-oxoethyl}ureido)phenylacetic acid;

(2RS,4SR,5RS)-3-(3-{2-[2-tert-butoxycarbonyl-5-(2-fluorophenyl)-4-(2-fluorophenyl)sulphonyl-1-pyrrolidinyl]-2-oxoethyl}ureido)benzoic acid;

(2RS,4SR,5RS)-3-(3-{2-[2-tert-butoxycarbonyl-5-(2-fluorophenyl)-4-(3-methoxyphenyl)sulphonyl-1-pyrrolidinyl]-2-oxoethyl}ureido)benzoic acid;

(2RS,4SR,5RS)-3-(3-{2-[2-tert-butoxycarbonyl-5-(2-fluorophenyl)-4-(4-methylphenyl)sulphonyl-1-pyrrolidinyl]-2-oxoethyl}ureido)benzoic acid;

(2RS,4SR,5RS)-3-(3-{2-[2-tert-butoxycarbonyl-5-(2-fluorophenyl)-4-(4-nitrophenyl)sulphonyl-1-pyrrolidinyl]-2-oxoethyl}ureido)benzoic acid;

(2RS,4SR,5RS)-3-(3-{2-[4-(4-aminophenyl)sulphonyl-2-tert-butoxycarbonyl-5-2(2-fluorophenyl)-1-pyrrolidinyl]-2-oxoethyl}ureido)benzoic acid;

(2RS,4SR,5RS)-3-(3-{2-[4-(4-acetamidophenyl)sulphonyl-2-tert-butoxycarbonyl-5-(2-fluorophenyl)-1-pyrrolidinyl]-2-oxoethyl}ureido)benzoic acid;

(2RS,4SR,5RS)-3-(3-{2-[2-tert-butoxycarbonyl-4-(4-dimethylaminophenyl)sulphonyl-5-(2-fluorophenyl)-1-pyrrolidinyl]-2-oxoethyl}ureido)benzoic acid;

(2RS,4SR,5RS)-3-(3-{2-[2-tert-butoxycarbonyl-5-(2-fluorophenyl)-4-methylsulphonyl-1-pyrrolidinyl]-2-oxoethyl}ureido)benzoic acid;

(2RS,4SR,5RS)-3-(3-{2-[4-(4-chlorophenyl)sulphonyl-5-(2-fluorophenyl)-2-isobutylcarbamoyl-1-pyrrolidinyl]-2-oxoethyl}ureido)phenylacetic acid;

(2RS,4SR,5RS)-3-(3-{2-[5-(2-fluorophenyl)-4-(2-fluorophenyl)sulphonyl-2-isobutylcarbamoyl-1-pyrrolidinyl]-2-oxoethyl}ureido)benzoic acid;

(2RS,4SR,5RS)-3-(3-{2-[5-(2-fluorophenyl)-2-isobutylcarbamoyl-4-(3-methoxyphenyl)sulphonyl-1-pyrrolidinyl]-2-oxoethyl}ureido)benzoic acid;

(2RS,4SR,5RS)-3-(3-{2-[5-(2-fluorophenyl)-2-isobutylcarbamoyl-4-(4-methylphenyl)sulphonyl-1-pyrrolidinyl]-2-oxoethyl}ureido)benzoic acid;

(2RS,4SR,5RS)-3-(3-{2-[5-(2-fluorophenyl)-2-isobutylcarbamoyl-4-(4-nitrophenyl)sulphonyl-1-pyrrolidinyl]-2-oxoethyl}ureido)benzoic acid;

(2RS,4SR,5RS)-3-(3-{2-[4-(4-aminophenyl)sulphonyl-5-(2-fluorophenyl)-2-isobutylcarbamoyl-1-pyrrolidinyl]-2-oxoethyl}ureido)phenylacetic acid;

(2RS,4SR,5RS)-3-(3-{2-[4-(4-acetamidophenyl)sulphonyl-5-(2-fluorophenyl)-2-isobutylcarbamoyl-1-pyrrolidinyl]-2-oxoethyl}ureido)benzoic acid; and (2RS,4SR,5RS)-3-(3-{2-[2-tert-butoxycarbonyl-5-(2-fluorophenyl)-morpholinosulphonyl-1-pyrrolidinyl]-2-oxoethyl}ureido)benzoic acid; or a salt thereof.

7. A process for preparing a compound of formula (I) according to claim 1 for which $R_5$ represents a phenylamino radical in which the phenyl ring may be substituted, said process comprising the steps of reacting a derivative of carbamic acid, which may be obtained in situ by the action of a derivative of carbonic acid selected from N,N'-carbonyldiimidazole, phosgene, diphosgene, triphosgene and p-nitrophenyl chloroformate on a derivative of formula:

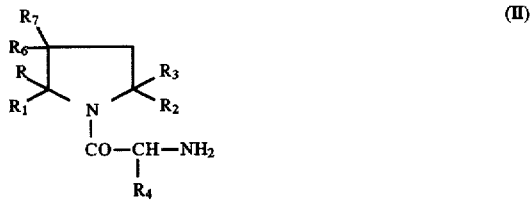

(II)

in which R, $R_1$, $R_2$, $R_3$, $R_4$, $R_6$ and $R_7$ have the same meanings as recited in claim 1, with an aniline in which the phenyl ring may be substituted with one or more substituents selected from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho,-alk-O—CO-alk,-alk-COOX,-alk-O-alk,-alk'-COOX, —O-alk-COOX, —CH=CH—COOX, —CO—COOX, -alk-$SO_3H$ in salt form, —CH=CH-alk', —C(=NOH)—COOX, —S-alk-COOX, —SO-alk-COOX, —$SO_2$-alk-COOX, —O—$CH_2$-alk'-COOX, —CX=N—O-alk-COOX, -alk-N (OH)—CO-alk, -alk-$SO_2H$, —$SO_2$—NH—CO—$R_{14}$, —$SO_2$—NH—$SO_2$—$R_{14}$, —CO—NH—CO—$R_{14}$, —CO—NH—$SO_2$—$R_{14}$, —B(OH)$_2$, —C(NH$_2$)=NOH, —$SO_2$—NH—$R_{15}$, —CO—NH—$R_{15}$,

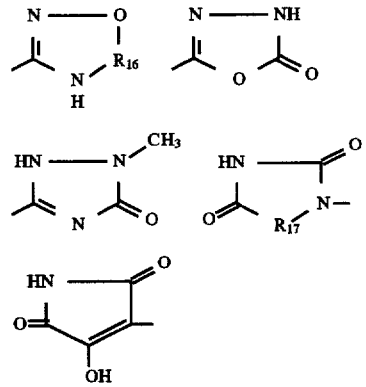

and 2,2-dimethyl-4,6-dioxo-1,3-dioxan-5-yl radicals; alk, alk', X, $R_{14}$, $R_{15}$, $R_{16}$ and $R_{17}$ having the same meanings as recited in claim 1;

isolating the product of said reaction; and optionally converting said isolated product into a salt.

8. A process for preparing a compound of formula (I) according to claim 1 for which $R_5$ represents a phenylamino radical in which the phenyl ring may be substituted with one or more substituents selected from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH=CH-alk', -alk-O-alk, trifluoromethylsulphonamido, -alk-$SO_3H$ in salt form, —O-alk-COOX, —CH=CH—COOX, —CO—COOX, —S-alk-COOX, —SO-alk-COOX, —$SO_2$-alk-COOX, —O—$CH_2$-alk'-COOX, —CX=N—O-alk-COOX, -alk-COOX and -alk'-COOX radicals in which X is an alkyl or phenylalkyl radical, said process comprising the steps of reacting a derivative of formula:

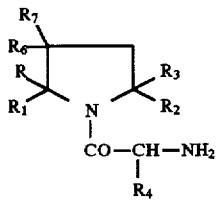 (II)

in which R, $R_1$, $R_2$, $R_3$, $R_4$, $R_6$ and $R_7$ have the same meanings as recited in claim 1, with a phenyl isocyanate in which the phenyl ring may be substituted with one or more substituents selected from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl,-alk-O—CO-alk, —CH=CH-alk',-alk-O-alk, trifluoromethylsulphonamido, -alk-$SO_3$H in salt form, —O-alk-COOX, —CH=CH—COOX, —CO—COOX, —S-alk-COOX, -SO-alk-COOX, —$SO_2$-alk-COOX, —O—$CH_2$-alk'-COOX, —CX=N—O-alk-COOX, -alk-COOX and -alk'-COOX radicals in which X is an alkyl or phenylalkyl radical; and alk and alk' have the same meanings as recited for formula (I) in claim 1;

isolating the product of said reaction; and optionally converting said isolated producted into a salt.

9. A process for preparing a compound of formula (I) according to claim 1 for which $R_5$ represents a phenyl radical which may be substituted or a naphthyl, indolyl or quinolyl radical, said process comprising the steps of reacting a derivative of formula:

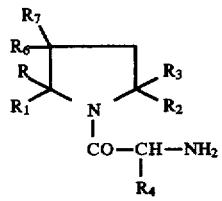 (II)

in which R, $R_1$, $R_2$, $R_3$, $R_4$, $R_6$ and $R_7$ have the same meanings as recited in claim 1, with an acid of formula HOOC-$R_5$, or a derivative thereof, in which $R_5$ has the same meaning as recited above;

isolating the product of said reaction; and optionally converting said isolated product into a salt.

10. A process for preparing a compound of formula (I) according to claim 1 for which $R_5$ represents a phenylamino radical in which the phenyl ring is substituted with a carboxyl radical or an -alk-COOX, —O-alk-COOX, -alk'-COOX, —CH=CH—COOX, —CO—COOX, —S-alk-COOX, —SO-alk-COOX, —$SO_2$-alk-COOX, —C(=NOH)—COOX, —O—$CH_2$-alk'-COOX or —CX=N—O-alk-COOX radical, and X represents a hydrogen atom, said process comprising the steps of hydrolyzing or hydrogenolyzing a compound of formula (I) for which X is an alkyl or phenylalkyl radical;

isolating the product of said hydrolyzation or said hydrogenolyzation; and optionally converting said isolated product into a salt.

11. A process for preparing a compound of formula (I) according to claim 1 for which $R_5$ represents a phenylamino radical in which the phenyl ring is substituted with a hydroxyiminoalkyl or alkoxyiminoalkyl radical, said process comprising the steps of reacting a compound of formula (I) for which $R_5$ represents a phenylamino radical in which the phenyl ring is substituted with an acyl radical, with a derivative of formula:

$$H_2N—OR_{20} \quad (IX)$$

in which $R_{20}$ represents a hydrogen atom or an alkyl radical;

isolating the product of said reaction; and optionally converting said isolated product into a salt.

12. A process for preparing a compound of formula (I) according to claim 1 for which $R_2$ represents a —$(CH_2)_n$—CO—$R_{10}$ chain; $R_{10}$ represents an alkoxy, cycloalkyloxy, cycloalkylalkyloxy or phenyl radical or a —$NR_{12}R_{13}$ radical; $R_7$ represents an alkylsulphonyl radical, a —$SO_2$—$NR_8R_9$ radical or a phenylsulphonyl radical in which the phenyl ring is substituted with one or more substituents selected from halogen atoms and alkyl, alkoxy, hydroxyl, nitro, amino, monoalkylamino, dialkylamino, acylamino, trifluoromethyl and trifluoromethoxy radicals; and $R_5$ represents a phenyl radical which may be substituted, a naphthyl, indolyl or quinolyl radical or a phenylamino radical in which the phenyl ring may be substituted with one or more substituents selected from halogen atoms and alkyl, alkoxy, alkylthio, trifluoromethyl, nitro, acyl, cyano, sulphamoyl, alkoxycarbonyl, carbamoyl, alkoxyiminoalkyl, alkoxyaminocarbonyl, -alk-O—CO-alk, —CH=CH-alk', -alk-O-alk, trifluoromethylsulphonamido, -alk-$SO_3$H in salt form, —O-alk-COOX, —CH=CH—COOX, —CO—COOX, —S-alk-COOX, —SO-alk-COOX, —$SO_2$-alk-COOX, —O—$CH_2$-alk'-COOX, —CX=N—O-alk-COOX, -alk-COOX and -alk'-COOX radicals, in which X is an alkyl or phenylalkyl radical, said process comprising the steps of reacting a derivative of formula:

 (IV)

in which $R_2$ and $R_7$ have the same meanings as recited above and R, $R_1$, $R_3$ and $R_6$ have the same meanings as recited in claim 1 with an acid of formula

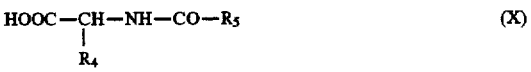 (X)

HOOC—CH—NH—CO—$R_5$
|
$R_4$ or a derivative thereof, in which $R_5$ has the same meanings as recited above, and $R_4$ has the same meanings as recited in claim 1;

isolating the product of said reaction; and optionally converting said isolated product into a salt.

13. A process for preparing a compound of formula (I) according to claim 1 for which $R_7$ represents a phenylsulphonyl radical in which the phenyl is substituted with an amino radical, said process comprising the steps of reducing a compound of formula (I) for which $R_7$ represents a phenylsulphonyl radical in which the phenyl is substituted with a nitro radical;

isolating the product of said reaction; and optionally converting said isolated product into a salt.

14. A process for preparing a compound of formula (I) according to claim 1 for which $R_7$ represents a phenylsulphonyl radical in which the phenyl is substituted with a monomethylamino radical, said process comprising the steps of methylating a compound of formula (I) for which $R_7$ represents a phenylsulphonyl radical in which the phenyl portion of said radical is substituted with an amino radical;

isolating the product of said methylation; and optionally converting said isolated product into a salt.

15. A pharmaceutical composition comprising a pharmaceutically effective amount of at least one compound of formula (I) according to claim 1, together with a pharmaceutically acceptable carrier.

* * * * *

UNITED STATES PATENT AND TRADEMARK OFFICE
CERTIFICATE OF CORRECTION

PATENT NO. : 5,716,936
DATED : February 10, 1998
INVENTOR(S) : CAPET et al.

It is certified that error appears in the above-identified patent and that said Letters Patent is hereby corrected as shown below:

On the Title Page, Item [75], line 2, under "Inventors", "Les Bains" should read --Enghein-les-Bains--.

On the Title Page, Item [57], below the Abstract, insert the following formula:

-- 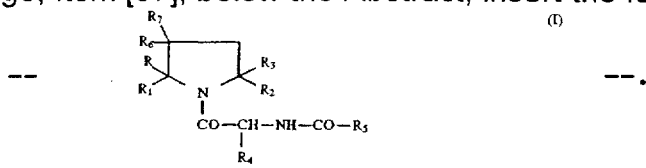 --.

Claim 1, column 37, line 58, "an quinolyl" should read --a quinolyl--.

Claim 4, column 39, line 44, before "and $R_{13}$", insert --$R_{12}$--.

Claim 6, column 41, line 27, "2(2-fluorophenyl)" should read --(2-fluorophenyl)--; line 61, after "fluorophenyl)", insert ---4--.

Claim 8, column 43, line 31, "producted" should read --product--.

UNITED STATES PATENT AND TRADEMARK OFFICE
CERTIFICATE OF CORRECTION

PATENT NO. : 5,716,936
DATED : February 10, 1998
INVENTOR(S) : CAPET et al.

It is certified that error appears in the above-identified patent and that said Letters Patent is hereby corrected as shown below:

Claim 14, column 45, line 9, "phe" should read --phe---.

Signed and Sealed this

Seventh Day of September, 1999

Attest:

Q. TODD DICKINSON

*Attesting Officer*    *Acting Commissioner of Patents and Trademarks*